(12) United States Patent
Mendez et al.

(10) Patent No.: US 7,083,971 B1
(45) Date of Patent: Aug. 1, 2006

(54) HYBRID YEAST-BACTERIA CLONING SYSTEM AND USES THEREOF

(75) Inventors: Michael Mendez, La Jolla, CA (US); Mitchell Finer, Woodside, CA (US)

(73) Assignee: Cell Genesys, Inc., South San Francisco, CA (US)

(*) Notice: Subject to any disclaimer, the term of this patent is extended or adjusted under 35 U.S.C. 154(b) by 290 days.

(21) Appl. No.: 09/762,476

(22) PCT Filed: Jun. 7, 2000

(86) PCT No.: PCT/US00/15588

§ 371 (c)(1), (2), (4) Date: Sep. 27, 2001

(87) PCT Pub. No.: WO00/75299

PCT Pub. Date: Dec. 14, 2000

Related U.S. Application Data

(60) Provisional application No. 60/137,974, filed on Jun. 7, 1999.

(51) Int. Cl.
*C12N 1/21* (2006.01)

(52) U.S. Cl. .............................. 435/252.33; 435/320.1

(58) Field of Classification Search ............ 435/320.1, 435/483, 488, 325, 91.4, 252.1; 536/23.1
See application file for complete search history.

(56) References Cited

U.S. PATENT DOCUMENTS

| | | | |
|---|---|---|---|
| 5,348,886 A * | 9/1994 | Lee et al. .................. | 435/69.1 |
| 5,378,618 A | 1/1995 | Sternberg et al. | |
| 5,434,066 A | 7/1995 | Bebee et al. | |
| 5,646,037 A * | 7/1997 | Buxton .................. | 435/252.33 |
| 5,744,336 A * | 4/1998 | Hodges et al. ........... | 435/320.1 |
| 5,866,404 A | 2/1999 | Bradshaw et al. | |
| 5,888,732 A | 3/1999 | Hartley et al. | |
| 6,828,093 B1 * | 12/2004 | Elledge et al. ................. | 435/6 |
| 2001/0014476 A1 * | 8/2001 | Crouzet et al. ............. | 435/455 |
| 2002/0170076 A1 * | 11/2002 | Dymecki ....................... | 800/8 |

OTHER PUBLICATIONS

Brunelli et al. A series of yeast/*Escherichia coli* Lambda epression vectors designed fro directional cloning of cDNAs and cre/lox-mediated plasmid excision. Yeast vol. 9:1309-1318, 1993.*

Liu et al. The univector plasmid-fusion system, a method fro rapic construction of recombinant DNA without restriction enzymes. Current Biology. vol. 8:1300-1309, 1998.*

Walmsley and Keenan, Eukaryote Alternative: advantages of using yeasts in place of bacteria in microbial biosensor development. (available at URL: gentronix.co.uk/keypapers/walmsleyBBEreview.pdf)(last visited Dec. 11, 2003).*

Whittle et al. Modern Microbial Genetics, Second Ed. Wiley-Liss, Inc. 2002; Chapter 17: 387-419.*

Storck et al., "Rapid construction in yeast of complex targeting vectors or gene manipulation in the mouse" Nucleic Acids Research (1996) 24(22):4594-4595.

Ripoll et al., "A new yeast artificial chromosome vector designed for gene transfer into mammalian cells" Gene (1998) 210(1):163-172.

Stratford-Perricaudet et al., "Widespread Long-term Gene Tranfer to Mouse Skeletal Muscles and Heart" J. Clin. Inves. (1992) 90:626-630.

Wivel et al., "Methods of Gene Delivery" Hematol. Oncol. Clin. North Am. 12(3):483-501.

Flotte et al., "Adeno-associated virus vectors for gene therapy" Gene Ther. (1995) 2(6):357-362.

Mittal et al., "Monitoring foreign gene expression by a human adenovirus-based vector using the firefly luciferase gene as a reporter" Virus Research (1993) 28:67-90.

Ketner et al., "Efficient manipulation of the human adenovirus genome as an infectious yeast artificial chromosome clone" Proc. Natl. Acad. Sci. (USA) (1994) 91:6186-6190.

Chartier et al., "Efficient Generation of Recombinant Adenovirus Vectors by Homologous Recombination in *E. coli*" Virol. (1996) 70:4805-4810.

Crouzet et al., "Recombinant construction in *E. coli* of infectious adenoviral genomes" Proc. Natl. Acad. Sci. (USA) (1997) 94:1414-1419.

He et al., "A simplified system for generating recombinant adenoviruses" Proc. Natl.Acad. Sci. (USA) (1998) 95:2509-2514.

(Continued)

*Primary Examiner*—James Ketter
(74) *Attorney, Agent, or Firm*—DLA Piper Rudnick Gray Cary

(57) ABSTRACT

A recombinational approach and system for the cloning, manipulation and delivery of large nucleic acids is disclosed. Vectors relying on homologous recombination to mediate the isolation, manipulation and delivery of large nucleic acid segments are disclosed.

2 Claims, 16 Drawing Sheets

OTHER PUBLICATIONS

Ioannou et al., "A new bacteriophage P1-drived vector for the propogation of large human DNA fragments" Nature (1994) 6:84-89.

Shizuya et al., "Cloning and stable maintenance of 300-kilobase pair fragments of human DNA in *E. coli* using an F-factor-based vector" Proc. Natl. Acad. Sci. (USA) (1992) 89:8794-9797.

Clark et al., "Isolation of yeast centromere and construction of functional small circular chromosomes" Nature (1990) 287:504-509.

Carbon, "Yeast Centomeres: Structure and Function" Cell (1984) 37:3551-3553.

Murray et al. "Construction of artificial chromosomes in yeast" Nature (1983) 305:189-193.

Hardy et al., "Construction of Adenovirus Vetcors through Cre-lox Recombination" J. Virol. (1997) 71(3):1842-1849.

Graham et al., "Characteristics of a Human Cell Line Transformed by DNA from Human Adenovirus Type 5" J. Gen. Virol. (1977) 36:59-72.

Wang et al., "A packaging cell line for propogation of recombinant adenovirusvectors containing two lethal gene-region deletions" Gene Therapy (1995) 2:775-785.

Fallaux et al., "Characterization of 911: A new helper cell line for the titeration and propogation of early region 1-deleted adenoviral vectors" Human Gene Therapy (1996) 7:215-222.

Burke et al., "Cloning of large segments of exogenous DNA into yeast by means of artificial chromosome vectors" Science (1987) 236:806-812.

Pierce et al., "A positive selection vector for cloning high molecular weight DNA by the bacteriophage P1 system: improved cloning efficacy" Proc. Natl. Acad. Sci. (USA) (1992) 89:2056-2060.

Wigler et al., "Transformation of mammalian cells with genes from procaryotes and eucaryotes" Cell (1979) 57:777-785.

Hirt, "Selective Extraction of Polyoma DNA from Infected Mouse Cell Cultures" J. Mol. Bio. (1967) 26:365-369.

* cited by examiner

SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 1
atcctgatca catcatcaat aatatacc                                          28

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
caagtatcgg gtatatacct actagtacgt                                        30

HYBRID YEAST-BACTERIA CLONING SYSTEM AND USES THEREOF

CONTINUING DATA

This application claims the benefit of U.S. Provisional Application No. 60/137,974, filed 7 Jun. 1999.

FIELD OF THE INVENTION

The invention relates to the capture, cloning, manipulation and delivery of large nucleic acids for a variety of genetic engineering purposes, including gene therapy. The invention further relates to novel recombinational cloning vectors and systems, and to methods of using same.

BACKGROUND OF THE INVENTION

Cloning vectors are important to understanding and manipulating various cellular processes and the underlying biochemical pathways. Such understanding enriches scientific knowledge and helps lead to new discoveries. Ultimately, such discoveries can lead to the development of valuable research tools and effective therapeutic compositions and treatments.

In stark contrast to the many vectors capable of manipulating short sequences, very few cloning vectors have been developed as tools for the genetic analysis, engineering and delivery of large nucleic acid sequences (e.g., entire genomes). The cloning and manipulation of complex sequences is inherently difficult due to the length of the inserts, which adversely affects the efficiency of the ligation reactions. Also, the scarcity of unique restriction sites further limits preparing large nucleic acids.

Those systems optimized for the analysis and manipulation of large nucleic acid sequences to date are ineffective for the delivery of such sequences to a target cell. Systems optimized for the delivery of large sequences also have been inefficient for analysis/manipulation of nucleic acids. For example, to prepare viral vectors containing a foreign gene, Stratford-Perricaudet et al. (*J. Clin. Invest.* 90:626–630, 1992) teach the use of homologous recombination to generate recombinant viruses in mammalian packaging cell lines.

Of the commonly used viral vectors, lentiviruses can be difficult to propagate and are relatively small (~9 kb). Thus, such vectors suffer from propagation difficulties and limited insert length capacity. (Wivel et al. (1998) *Hematol. Oncol. Clin. North Am.* 12(3):483–501). A limited insert size has the added drawback of perhaps preventing the addition of regulatory sequences.

Similarly, AAV-based vectors, because of relatively small size (~4.5 kb) are limited greatly in the maximum insert size. (Flotte et al. (1995) *Gene Ther.* 2(6):357–362).

Adenovirus-based vectors offer several attractive features including ease of propagation, high level of transgene expression, lack of integration in the host genome, which lowers the risk of mutagenesis, and the ability of carrying larger inserts (~35 kb) (Hardy et al. (1997) *J. Virol.* 71(3): 1842–1849).

Some efforts to develop recombinant adenoviruses employed three different approaches that rely on homologous recombination in either mammalian cells, yeast cells or bacterial cells.

Homologous recombination in mammalian cells is the most widely applied. Mittal et al. (*Virus Research* 28:67–90, 1993) teach the co-transfection of two plasmids containing a split defective genome into a complementary packaging cell line capable of rescuing the defective adenovirus.

However, as noted above, homologous recombination in mammalian cells is a rare event. Thus, the use of mammalian cells can be inefficient. The mammalian cell approach also requires repeated rounds of plaque purification as well as complex and time consuming viral production protocols. In addition, because the introduction of specific mutations in the regions of the vectors other than the ends of the adenoviral sequences is extremely tedious, engineering and recovering multiple mutations in the recombinant vector is virtually impossible.

Ketner et al. (*Proc. Natl. Acad. Sci.* 91:6186–6190, 1994) teach a yeast-based system in which the full length adenovirus genome was cloned and maintained as an infectious yeast artificial chromosome. That system relied on the high homologous recombination rate in yeast to modify any sequence within the vector and to introduce multiple inserts as needed. However, the low efficiency of formation of the recombinant vector and the low yield of the recombinant vector from yeast cells severely limit the ability to rescue virions, thus making transfection very difficult.

Attempts to overcome the limitations of the yeast-based system lead Chartier et al. (*Virol.* 70:48054810, 1996), Crouzet et al. (*Proc. Natl. Acad. Sci.* 94:1414–1419, 1997) and He et al. (*Proc. Natl. Acad. Sci.* 95:2509–2514, 1998) to develop bacterial systems. Bacterial systems offer the advantage of higher recombination rates and thus are more efficient.

However, those systems require large, cumbersome screening processes to identify recombinant clones. Other considerable limitations are the inability to engineer multiple mutational inserts and the need for highly specific bacterial shuttle vectors for each specific bacterial system.

Thus, there remains a yet unfulfilled need for versatile recombinatorial vectors and methods capable of overcoming the shortcomings of existing approaches. Such vectors and methods should be capable of broad targeting range of both dividing and non-dividing cells, and high levels of transgene expression. Ideally, such systems would have high recombination rates while minimizing the risk of integration in the host genome. To address present needs, such systems should allow the manipulation of large sequences and engineering multiple mutational inserts, while minimizing the need for extensive screening protocols. Such vectors also should be propagated easily and allow the recovery of sufficient amounts for the delivery of such recombinant nucleic acids directly to mammalian cells in vitro or in vivo.

SUMMARY OF THE INVENTION

The instant invention provides a versatile, recombinational approach to the capture, cloning, manipulation, production and delivery of large nucleic acids to target cell. The invention provides a recombinational cloning system. More specifically, the invention provides vectors, relying on homologous recombination technologies, to mediate the isolation, manipulation and delivery of large nucleic acid segments to a cell or virus. The invention also provides methods for using such recombinational cloning vectors to clone, to manipulate and to deliver large nucleic acids. Additionally, the invention provides methods for using such recombinational cloning systems as potentiators of transgenic plant and animal studies, and for plant as well as animal genetic engineering approaches, such as, for example, gene therapy and vaccine applications.

In a first aspect, the invention provides a recombinational cloning system that includes: (a) a first arm containing a first selectable marker and a first cyclization element; and (b) a second arm containing a second selectable marker and a second cyclization element. At least one arm also includes an origin of replication. In another preferred embodiment of the invention, each arm also includes a rare restriction endonuclease recognition site. In yet another preferred embodiment of the invention, each arm contains a polylinker. The first cyclization element of may be a nucleic acid sequence including a first LoxP site and the second cyclization element may be a nucleic acid sequence including a second LoxP site.

In one preferred embodiment, the invention provides a recombinational cloning system that includes: (a) a first arm containing a first selectable marker, a first cyclization element and a first nucleic acid homologous to the 5' terminus sequence of a target nucleic acid; and (b) a second arm containing a second selectable marker, a second cyclization element and a second nucleic acid homologous to the 3' terminus of the target nucleic acid.

The invention also provides a composition including the recombinational cloning system according to the invention and a target nucleic acid. In one embodiment of the invention, the target nucleic acid is a eukaryotic nucleic acid. In an embodiment of the invention, the target nucleic acid is a mammalian nucleic acid. In a preferred embodiment, the target nucleic acid is a human nucleic acid. In another preferred embodiment, the target nucleic acid is a viral nucleic acid.

In one embodiment, all of the elements of interest are contained on a single molecule, such as, a circle, which includes a plasmid or an episome. Thus, in another aspect, the invention provides a recombinational cloning vector that comprises a yeast selectable marker, a bacterial selectable marker, a telomere, a centromere, a yeast origin of replication, a bacterial origin of replication and a rare restriction endonuclease recognition site. In one embodiment of the invention, the vector contains at least one unique cloning site. In a preferred embodiment, the vector contains a polylinker. As will become apparent herein, the vector readily is engineered to facilitate the introduction of nucleic acids homologous to nucleic acids flanking a target nucleic acid, by conventional genetic engineering methods. Hence, in one embodiment, the invention provides a cloning vector that includes a first nucleic acid homologous to the 5' terminus of a target nucleic acid; and a second nucleic acid homologous to the 3' terminus of the target nucleic acid.

In another aspect, the invention provides a method of producing a gap-filled vector containing a target nucleic acid. In that method, a target nucleic acid, a first arm comprising a first nucleic acid homologous to the 5' terminus of the target nucleic acid, a first selectable marker and a first cyclization element, and a second arm comprising a second nucleic acid homologous to the 3' terminus of the target nucleic acid, a second selectable marker and a second cyclization element are contacted under conditions which allow homologous recombination. The method according to that aspect of the invention produces a gap-filled vector by homologous recombination among the two arms and the target nucleic acid. In an embodiment according to that aspect of the invention, at least one arm further comprises an origin of replication. In another preferred embodiment of the invention, each arm further comprises a rare restriction endonuclease recognition site. In a more preferred embodiment of the invention, the first cyclization element is a nucleic acid having a first LoxP site and the second cyclization element is a nucleic acid having a second LoxP site.

In one preferred embodiment, homologous recombination is performed in vitro. In a particularly preferred embodiment of that aspect, homologous recombination is performed in vivo. In a more preferred embodiment, homologous recombination occurs in a yeast cell. In one preferred embodiment, homologous recombination occurs in *Saccharomyces cerevisiae*, *Saccharomyces pombe* or *Saccharomyces ustillago*.

In another aspect, the invention provides a eukaryotic host cell harboring the recombinational cloning system or vector according to the invention. In one embodiment, the eukaryotic host cell is a yeast cell. In one preferred embodiment of the invention, the yeast cell is *Saccharomyces cerevisiae*, *Saccharomyces pombe* or *Saccharomyces ustillago*.

In yet another aspect, the invention provides a method of circularizing the gap-filled arms of the invention. In one embodiment of the invention, the gap-filled vector is circularized by contacting the first and the second LoxP sites with Cre, thereby producing a circularized gap-filled vector by site-specific recombination. In a preferred embodiment, the gap-filled vector is circularized in bacteria. In another preferred embodiment, the gap-filled vector is circularized in vitro. The invention further provides a bacterial cell comprising the circularized gap-filled vector of that aspect of the invention.

In a further aspect, the invention provides methods for producing a recombinant delivery unit including the steps of: (a) producing a gap-filled vector containing a target nucleic acid; and (b) introducing the gap-filled vector in a delivery unit. In one embodiment of the invention, the delivery unit is a virus. Hence, introduction of the gap-filled vector is effected by introducing the vector of step (a) in a complementing mammalian cell to generate a replication deficient viral vector. The vector may be linear or circularized prior to introduction in the delivery unit.

In an additional aspect, the invention provides novel recombinational cloning systems and methods useful to investigate the role of specific nucleic acids in a given virus or mammalian cell type. The vectors and methods appropriate to the invention are essentially the same as discussed for the preceding aspects of the invention.

In other aspects, the invention provides recombinational cloning systems and methods of using same, useful for the cloning, manipulation and delivery of nucleic acids. In some embodiments of the invention, the vectors and methods are used for therapeutic or diagnostic purposes including gene transfer both in vitro and in vivo, as well as vaccination in vivo, and other gene therapy applications. In other preferred embodiments, the vectors and methods of the invention are used for viral, plant, bacterial, nematode, fish, fly, mammalian, as well as animal molecular genetic engineering. Hence, in some preferred embodiments, the invention provides tools and methods for target validation of genes identified through functional genomics approaches and for the construction of libraries of mammalian genes to be inserted at any given location in a genome.

BRIEF DESCRIPTION OF THE DRAWINGS

Aspects of the foregoing and other objects of the invention, the various features thereof, as well as the invention itself are provided in the following description, including the accompanying drawings.

In the figures, the following abbreviations are used: HIS3: yeast HIS3 gene; TRPI: yeast TRPI gene; URA3: yeast URA3 gene; ADE1: yeast ADE1 gene; LYS2: yeast LYS2 gene; TEL: yeast telomere; CEN: yeast centromere; ARS: autonomously replicating sequences, yeast origin of replication; 5FOA: 5-fluoroorotic acid; mµ or mu: map unit; AMP: ampicillin resistance determinant; KAN: kanamycin resistance determinant; Ori: ColE1 origin of replication; LOX: LoxP site; Adeno: Adenovirus; PCR: polymerase chain reaction; PFG: Pulsed field gel; CMV: cytomegalovirus; E1, E2 and E4: portions of the adenovirus genome; Δ: deletion; GFP: green fluorescent protein; P1: a bacterial artificial chromosome; CRE: Cre recombinase; REP: an origin of replication; ψ: a virus packaging signal; POLY AA: a polyadenylation site; ITR: inverted terminal repeats; and PF: pulsed field. A number of restriction endonuclease sites are indicated using the known designations, such as SnaBI, XhoI, NotI, I-SceI, I-PpoI and so on.

Figure 1:
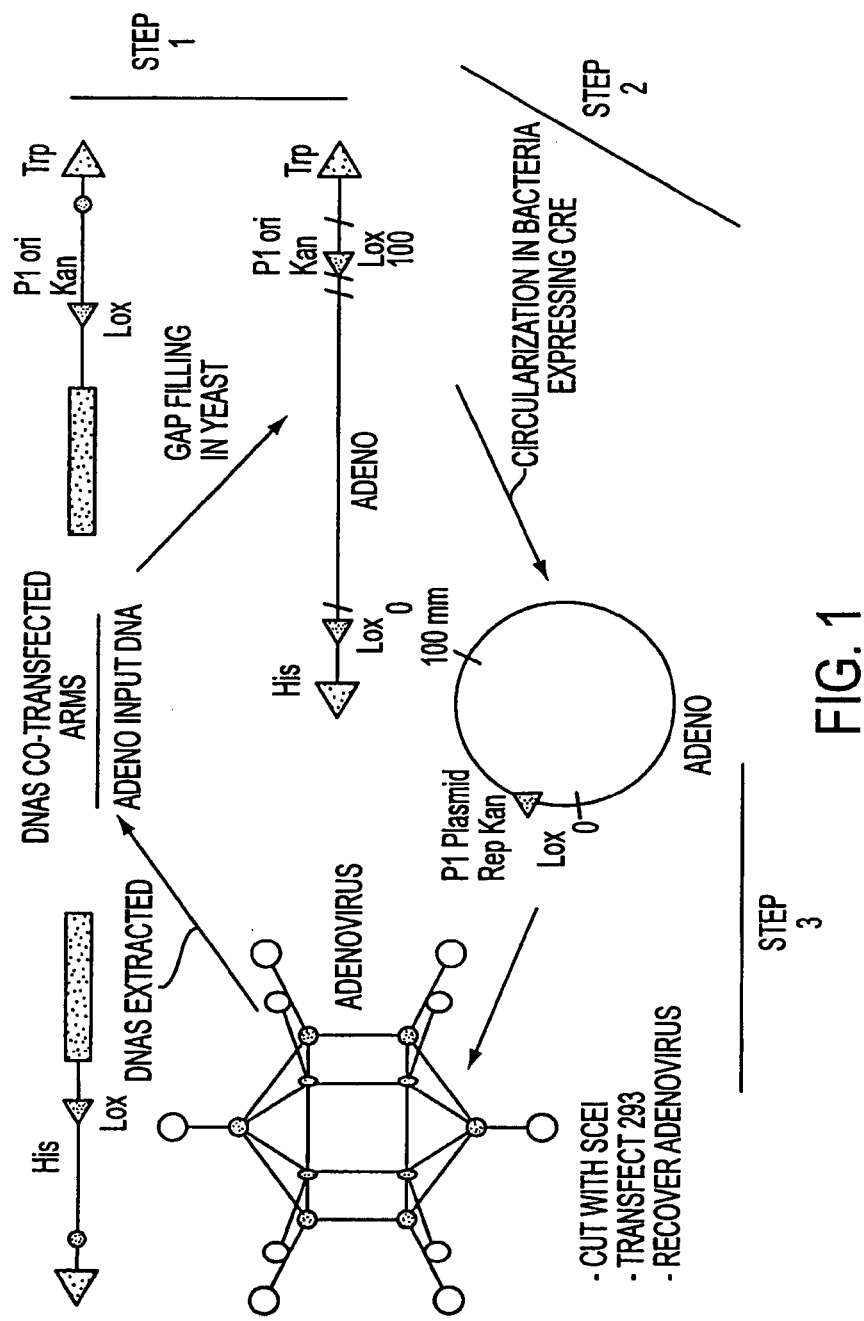

FIG. 1 depicts a representative DNA cloning system according to the invention. Step 1 shows homologous recombination in a yeast cell to capture, clone and manipulate large DNA as a gap-filled vector. Step 2 shows the use of a representative cyclization element, LoxP, to promote Cre-Lox recombination in bacteria to convert the linear construct to a circularized functional nucleic acid, which can be amplified and purified in bacteria. In turn, if the vectors are derived from a viral genome (i.e., adenovirus) or are engineered to contain the pertinent viral elements, Step 3 illustrates the bacterial cells can be treated to release the viral genome and allow the recovery of infectious viral particles.

Figure 2:
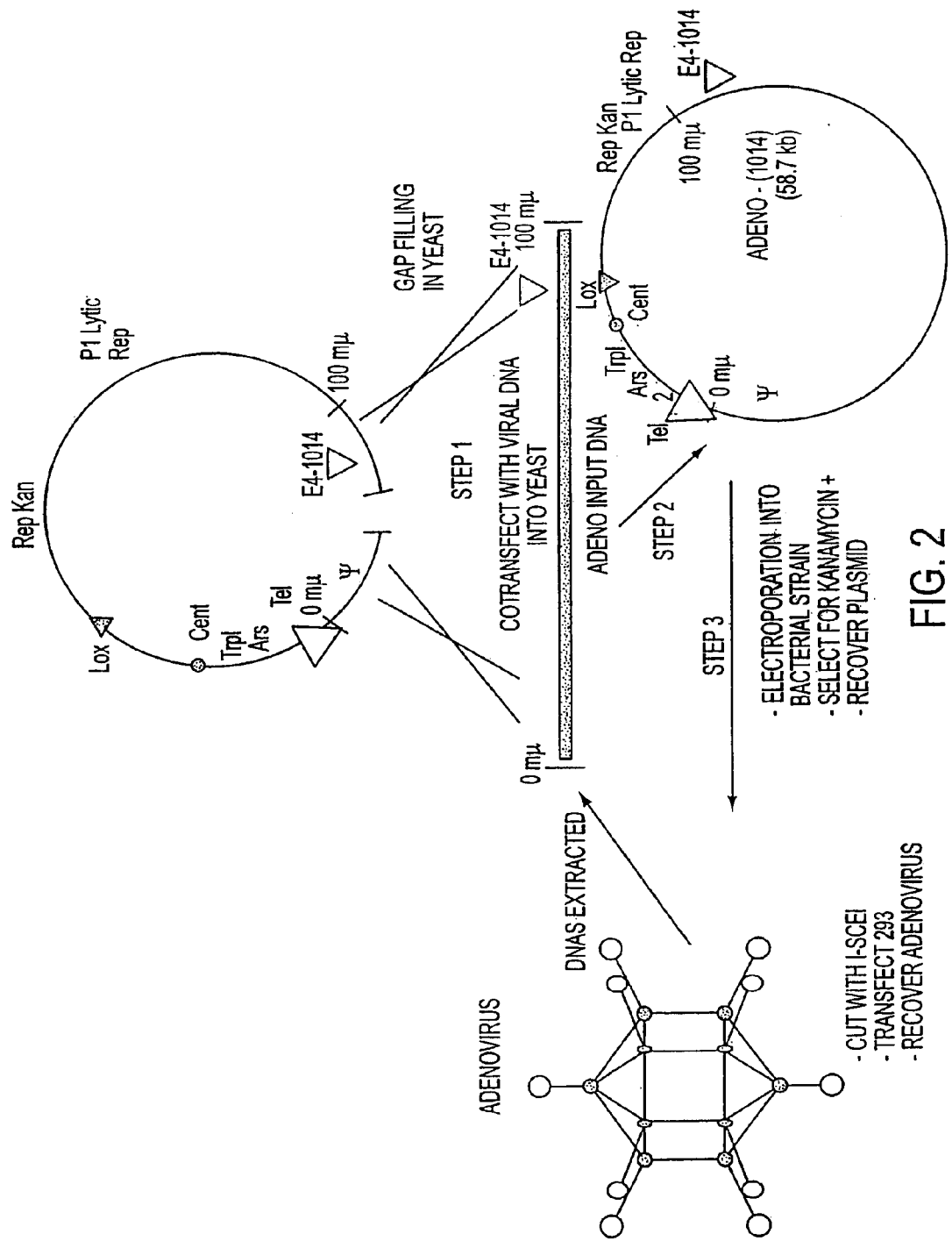

FIG. 2 depicts a representative circular vector according to the invention. Step 1 shows homologous recombination in a yeast cell to capture, clone and manipulate large amounts of DNA as a gap-filled vector. Step 2 illustrates the ability of the gap-filled vector to be amplified and purified in bacteria. In turn, if the vector is derived from a viral genome (e.g., adenovirus as shown) or is engineered to contain the pertinent viral elements, Step 2 illustrates that the vector can be cut to release the viral genome and allow the recovery of infectious viral particles (e.g., adenovirions as shown).

Figure 3:
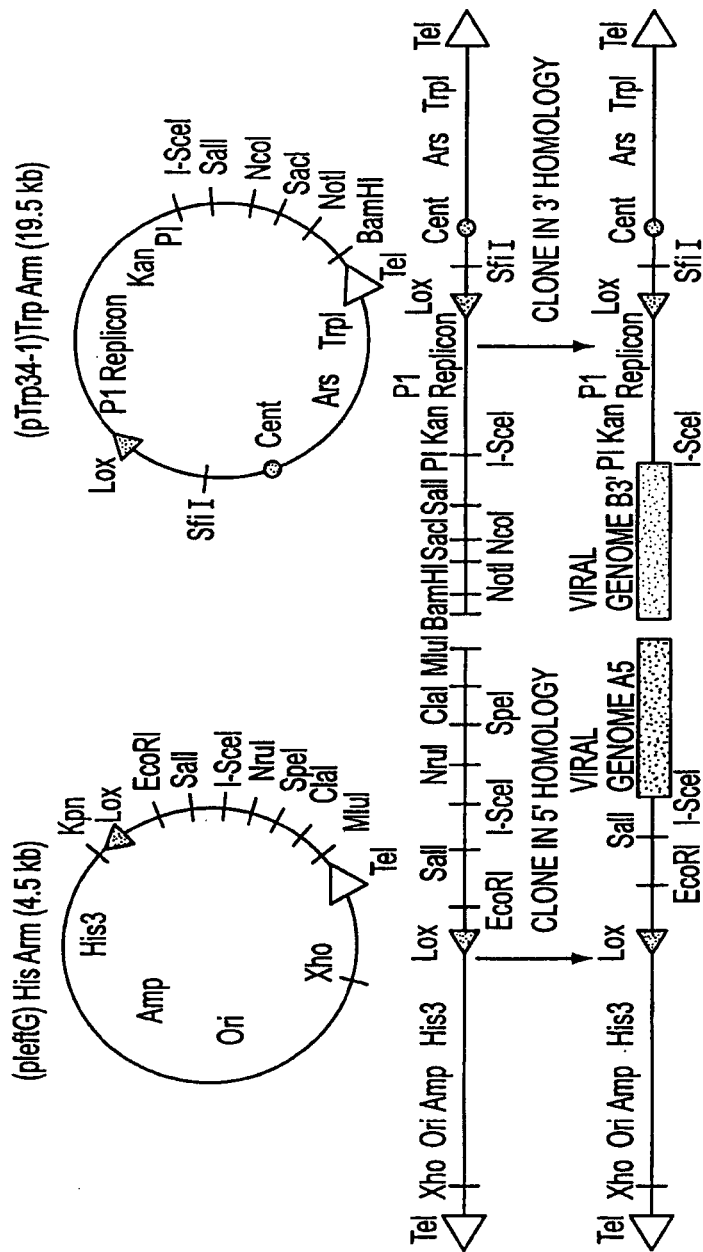

FIG. 3 depicts a representative cloning system according to the invention. The cloning system comprises a left arm (designated pleftG) and a right arm (designated pTrp34-I).

Figure 4:
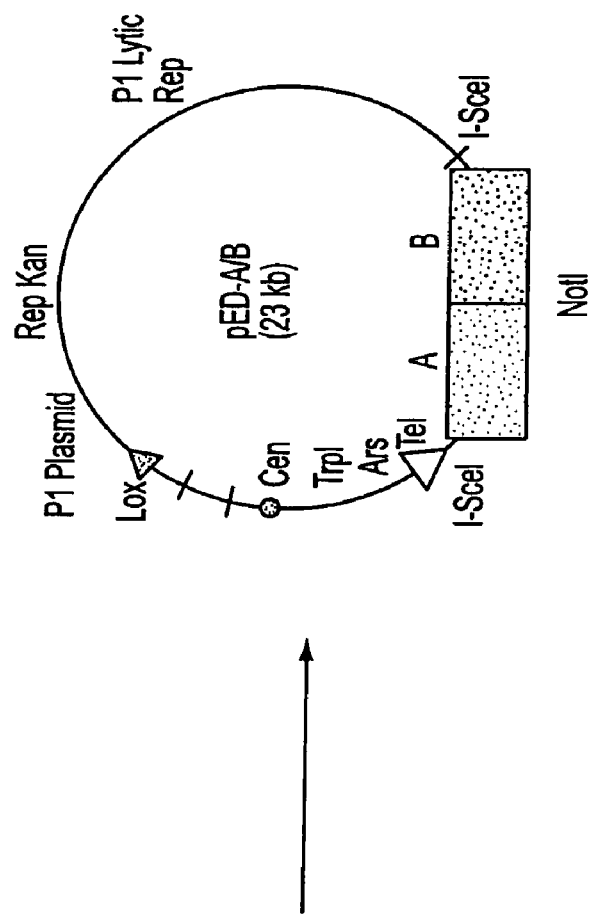
Figure 4:
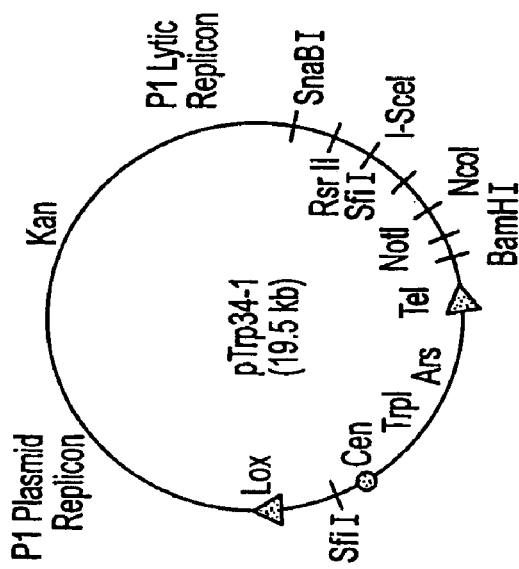

FIG. 4 depicts the preparation of a representative vector for the manipulation of a target sequence containing sequences homologous to sequences A and B in the 5' and the 3' termini. The representative vector, i.e., Trp34-1, includes TRPI, LoxP site, I-SCEI site, P1 plasmid replicon ori, P1 lytic replicon, KAN, a bacterial selectable marker, ARS, CEN, TEL and a polylinker in which 5'-A and 3'-B homologous sequences can be cloned, as schematically shown. The 5'-A and the 3'-B homologous sequences are separated by a NotI recognition site to be used to linearize the vector for gap-filling in yeast.

Figure 5:
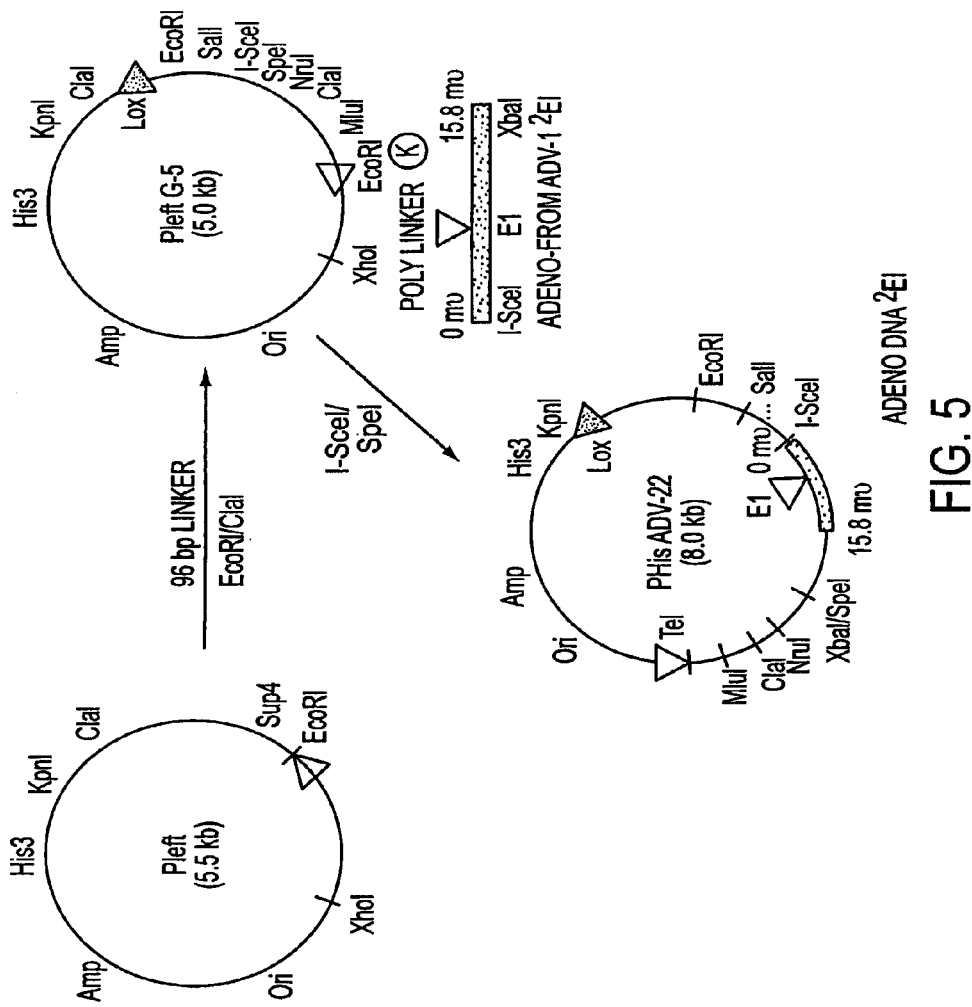

FIG. 5 depicts a representative left arm according to the invention. A linker was cloned into Pleft, which included seven unique cloning sites, a LoxP site and an I-SceI recognition site. The resultant construct, PleftG-5, includes HIS3, Telomere (clear triangle), LoxP site and a rare cutter recognition site. PHis ADV-22 may also be used according to the invention in conjunction with delivery units such as adenoviral particles.

Figure 6:
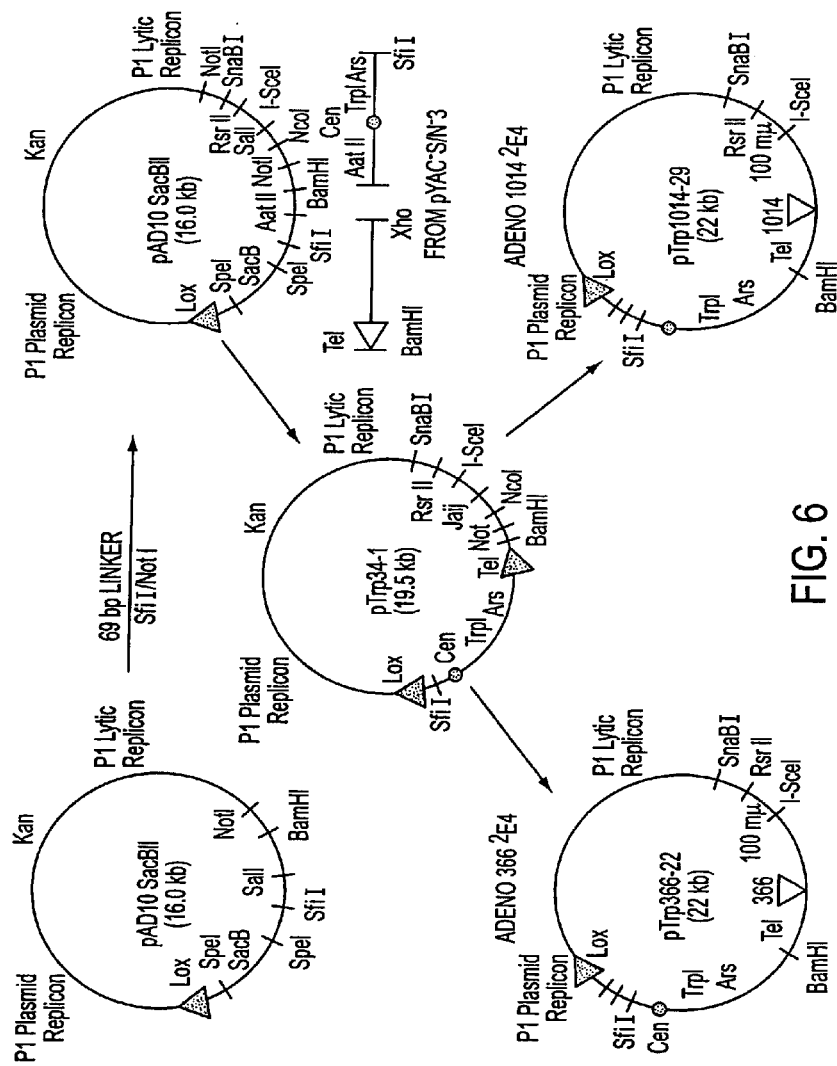

FIG. 6 depicts a representative right arm according to the invention. The representative right arm, pTrp 34-1, comprises TRPI, telomere, centromere, ARS, I-SceI site, P1 plasmid replicon, KAN, P1 lytic replicon, four unique cloning sites and a LoxP site, for a gap-filling arm. pTrp 1014-29 and pTrp 366-22 both were obtained by PCR amplification of the 1.5 kb of the 3' end of either AD5-1014 or AD5-366, and cloning into pTrp 34-1.

Figure 7:
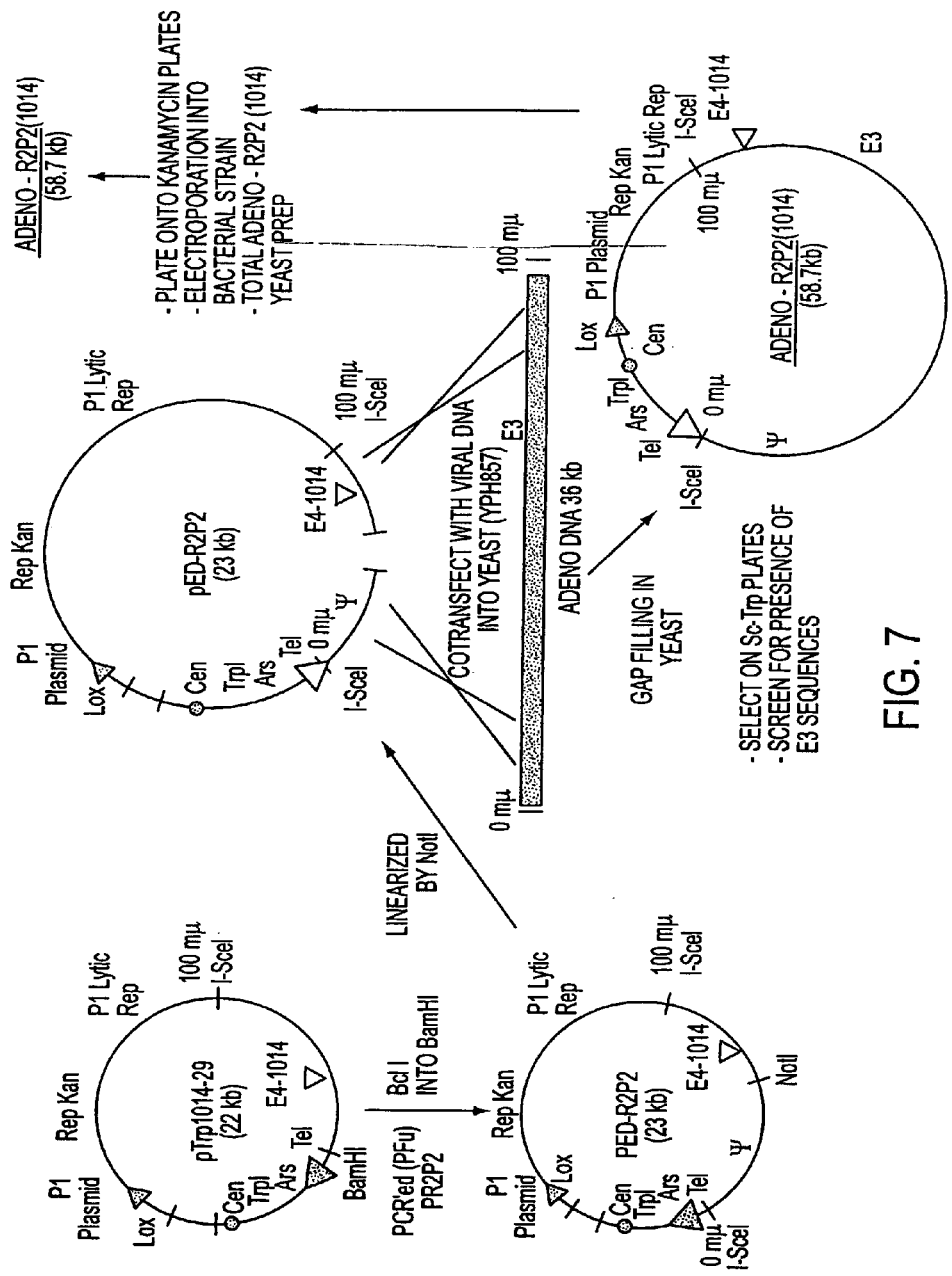

FIG. 7 depicts a representative vector, pED-R2P2, useful to introduce the 1014 E4 deletion in the Ad5 virus.

Figure 8:
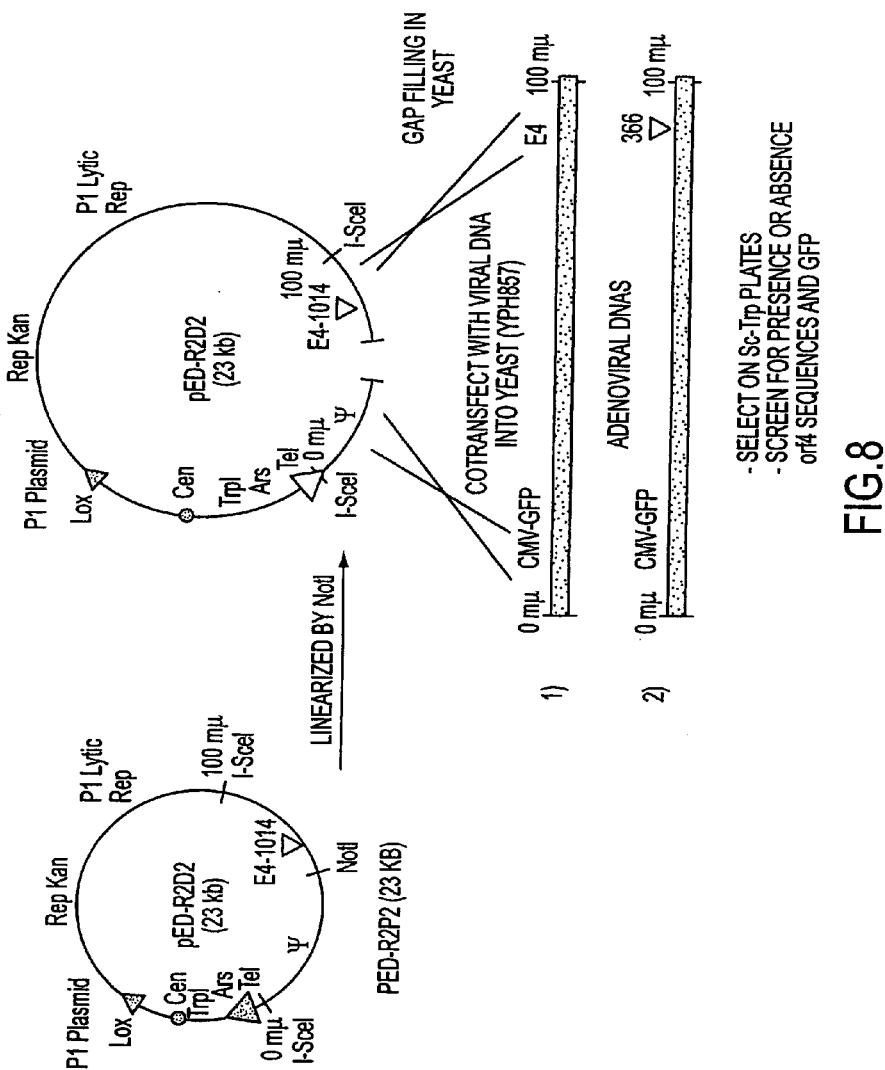

FIG. 8 depicts the construction of Ad5 constructs using a representative vector, pED-R2D2, containing the 3' end of homology and the E4 deletion, Ad510T4 together with the 5' end of homology derived from the pR2P2 construct.

Figure 9:
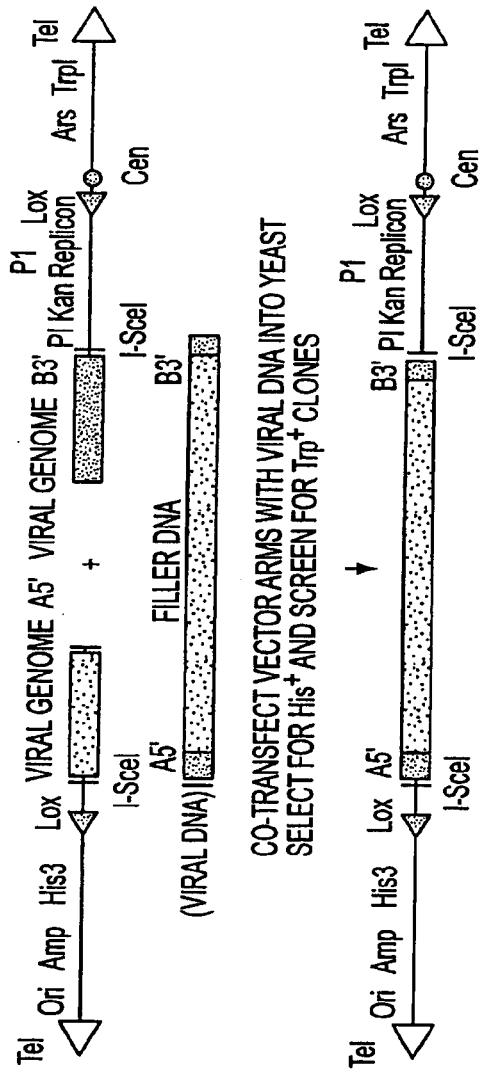

FIG. 9 depicts producing representative gap-filled vectors according to the invention. Using homologous recombination in yeast, three overlapping homologous pieces as shown are reconstructed into a yeast artificial chromosome in yeast. The gap-filled vector is maintained and stable if both arms, HIS+(TEL) and TRP+(CEN, ARS, TEL), are present and functional.

Figure 10:
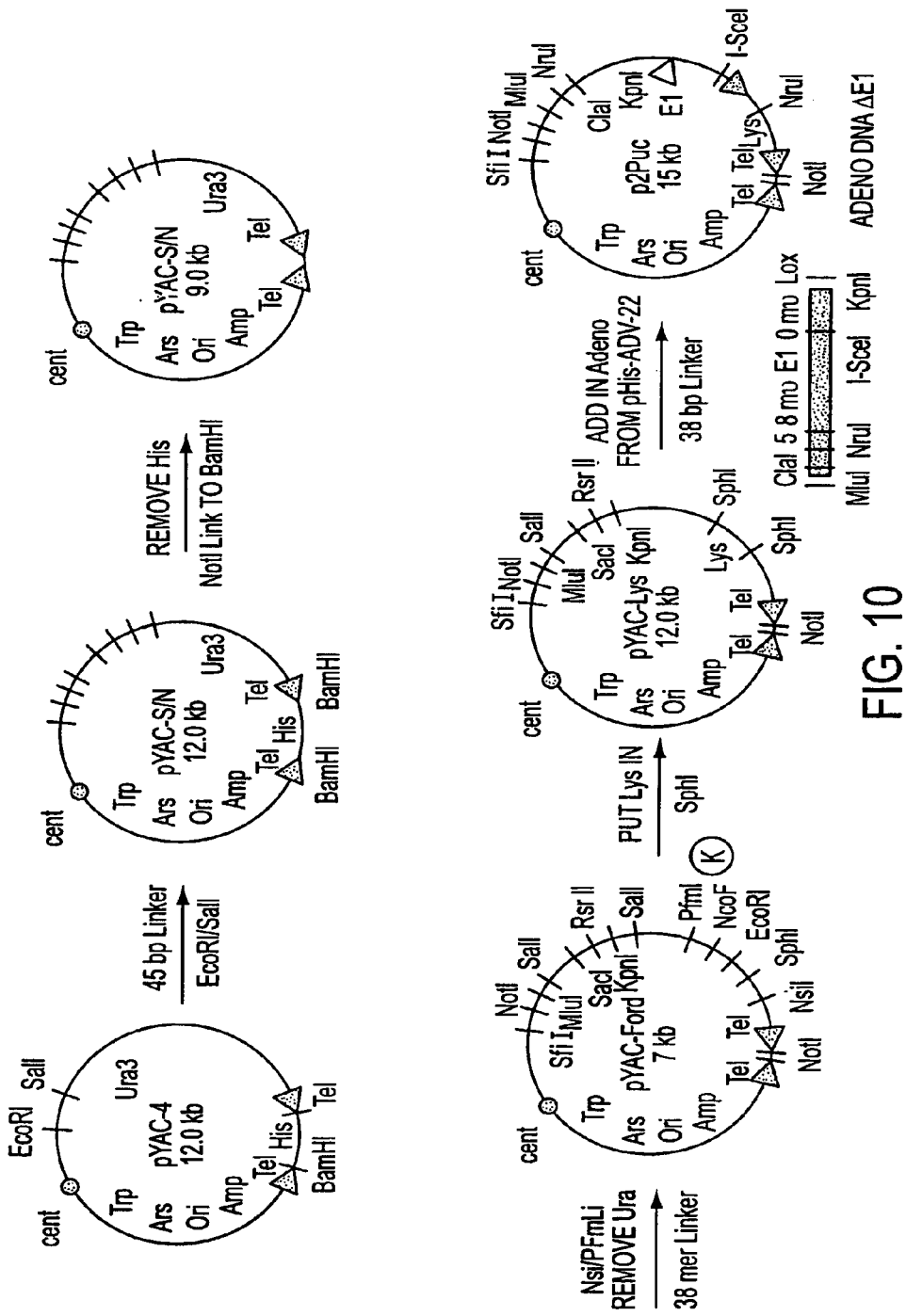

FIG. 10 is a diagrammatic representation of the construction of the arm replacement plasmid p2Puc. As shown in the diagram, the following steps were accomplished: (i) a 45 bp linker was cloned into pYAC-4, (ii) the His3 gene was removed, (iii) the Ura3 gene was removed, (iv) the yeast marker LYS2 was inserted and (v) the 5' end of Ad5 was inserted. The resultant construct, p2Puc, includes LYS2, a telomere, LoxP site, rare cutter recognition site and the 5' end of Ad5. p2Puc may be used to modify the 5' end of gap-filled adeno vectors.

Figure 11:
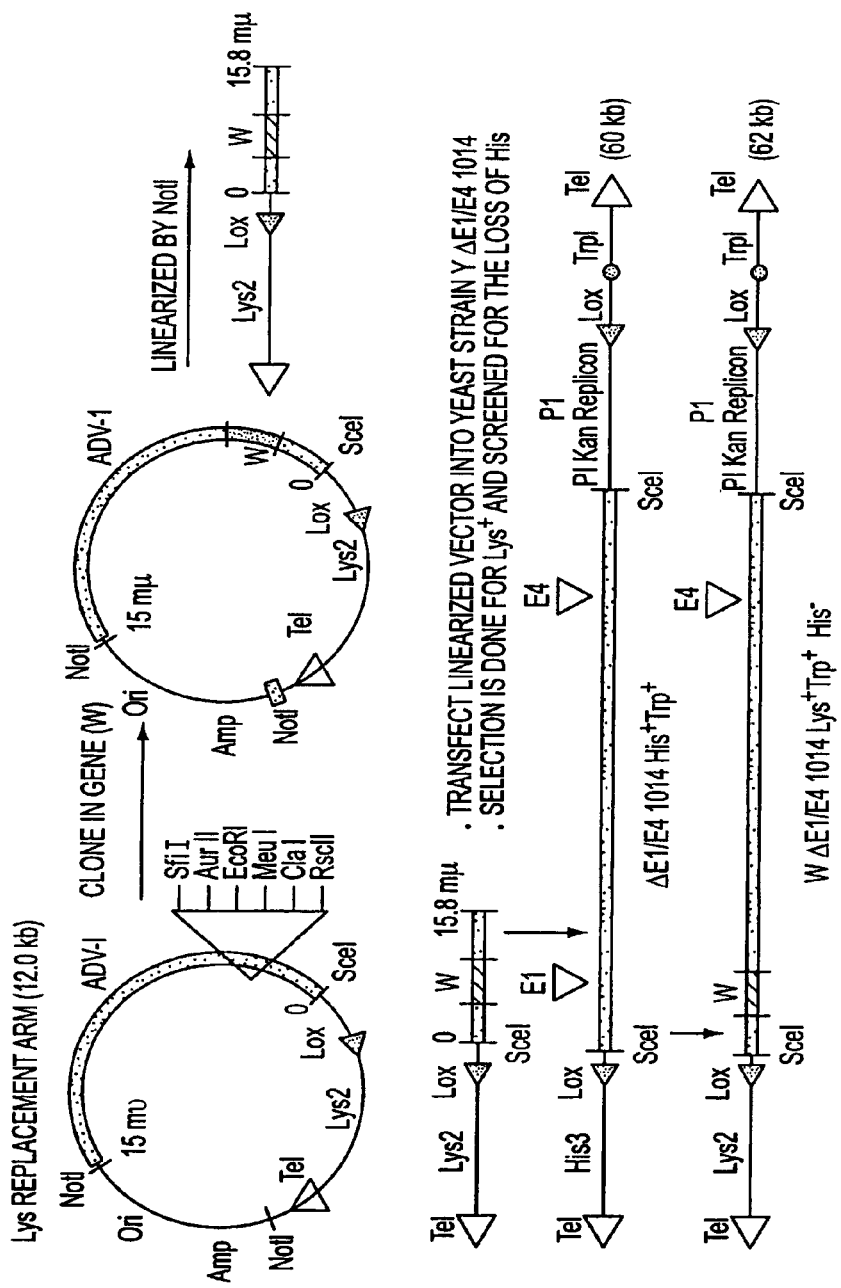

FIG. 11 is a diagrammatic representation of the process of viral arm replacement. Plasmid p2Puc is used to modify the HIS3 arm of a gap-filled adeno vector. According to that aspect of the invention, p2Puc is used to move a transgene into the E1 region of an adeno vector. The vector may be used to move a transgene into or introduce an E1 deletion in the Ad genome.

Figure 12:
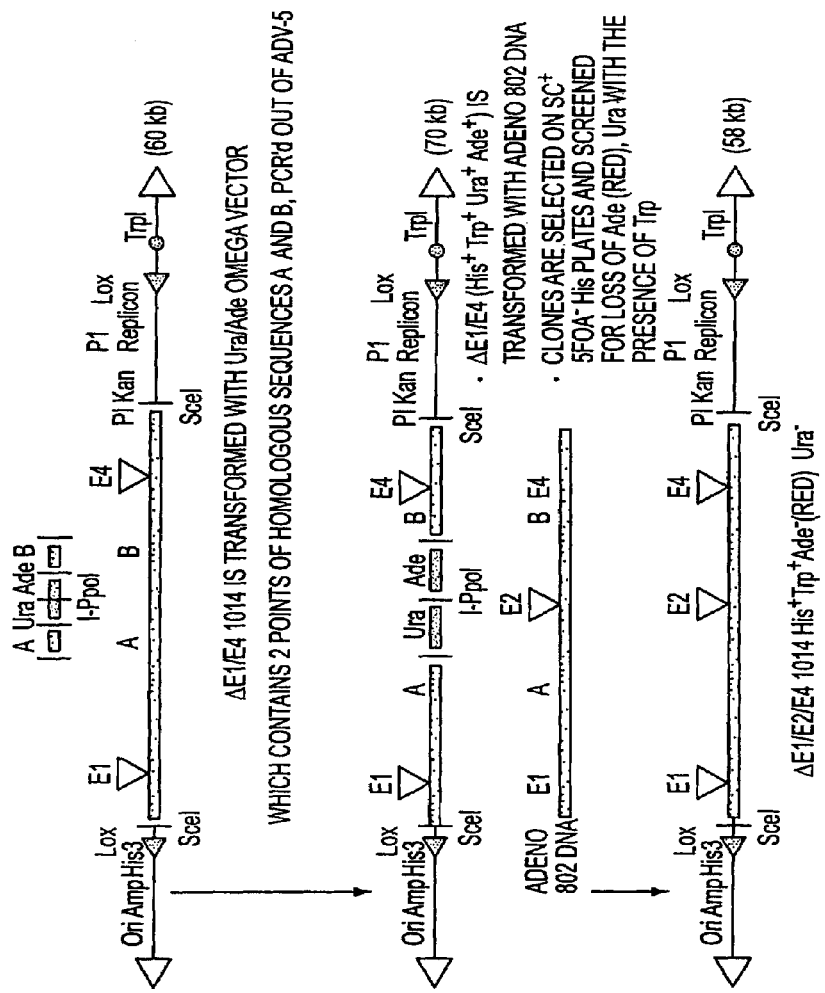

FIG. 12 is a diagrammatic representation of a method according to the instant invention by which mutations can be introduced into a vector without the use of selection against the yeast marker on the arms. As exemplified, the method according to the invention is a versatile approach to the manipulation of vectors. In the example, an ex vivo mutagenized yeast strain was used to make a mutation in the middle of a vector.

Figure 13:
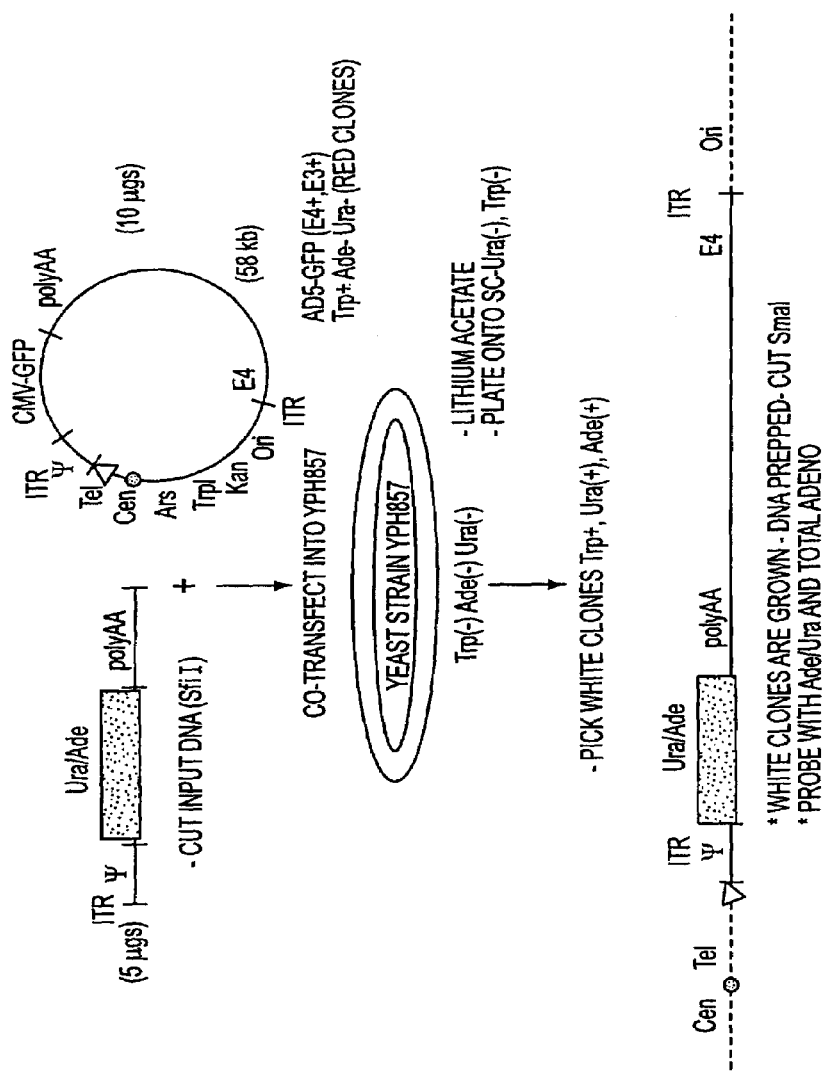

FIG. 13 is a diagrammatic representation showing the use of the methods and the vectors of the invention to modify the E1 region of a gap-filled circular vector.

Figure 14:
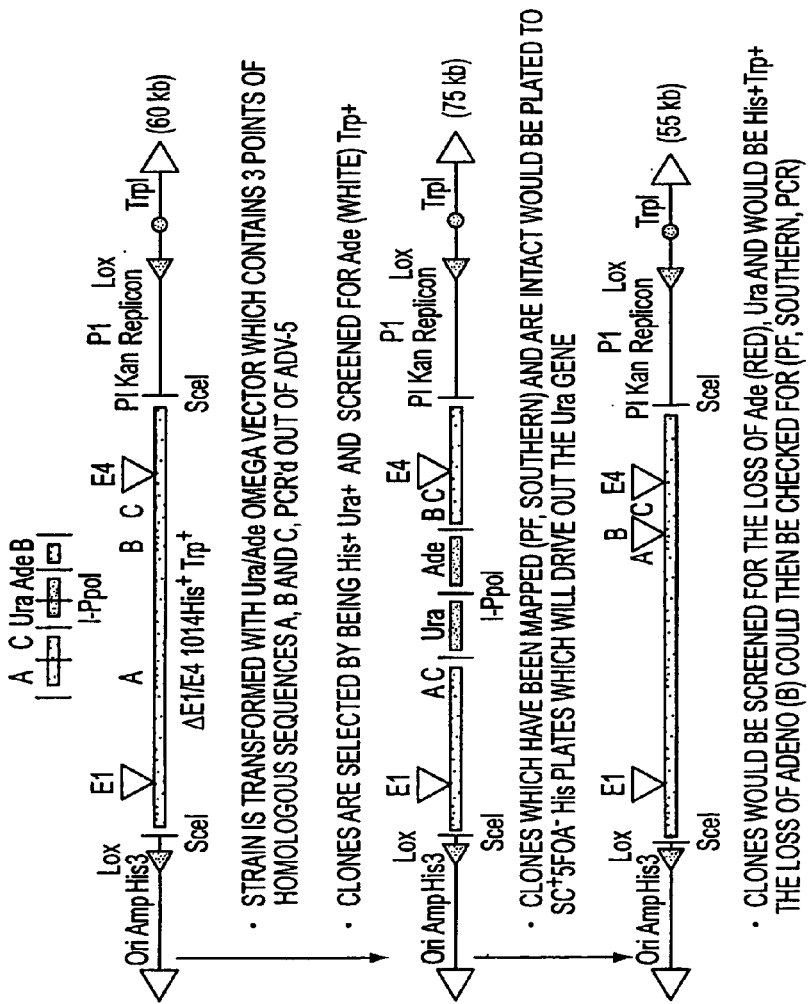

FIG. 14 is a diagrammatic representation of a method according to the invention whereby a mutation can be introduced into a vector without the use of selection against the arms and in which the mutation has not been made ex vivo of the yeast (cloned). In the diagram, a novel deletion (del B) was made by targeting a tandem duplication (C) and by the removal of the URA3 and ADE1 yeast markers by negative selection of 5FOA on the URA3 yeast marker.

Figure 15:
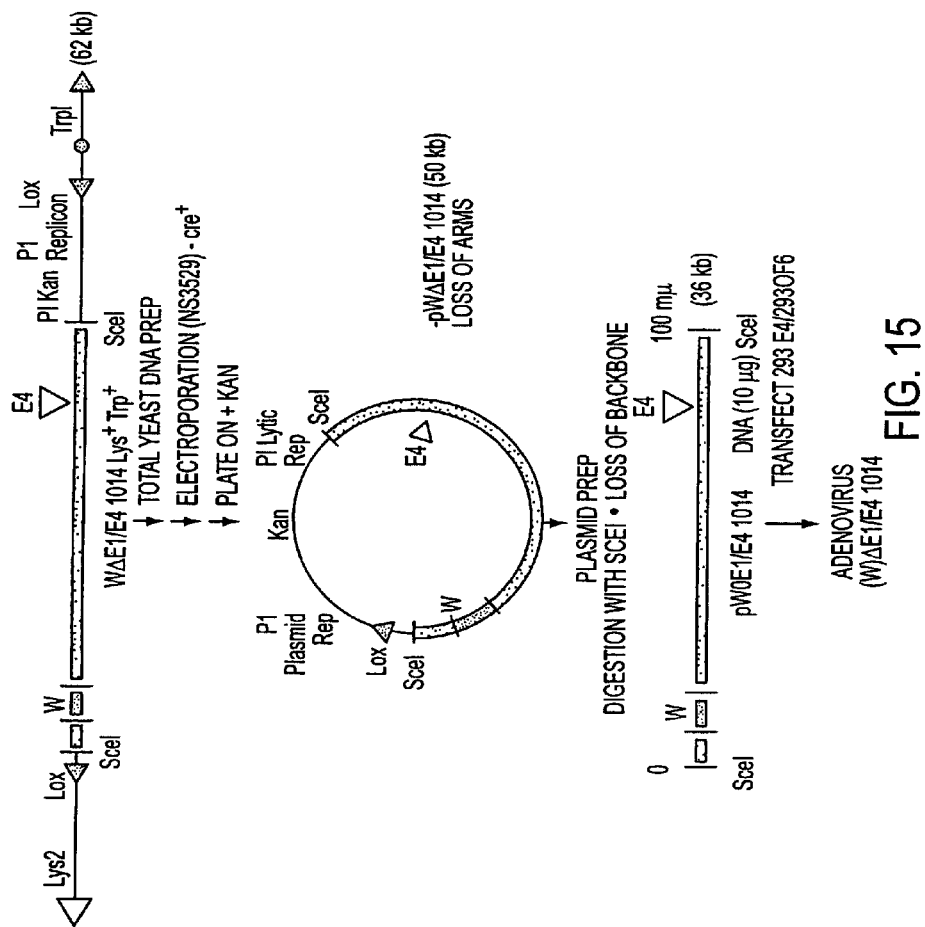

FIG. 15 is a diagrammatic representation of a method of the invention whereby a gap-filled vector is (a) circularized by Cre-Lox recombination in a bacterial strain expressing Cre protein; (b) amplified and purified in bacteria according to conventional protocols; and (c) transferred into a complementing cell line following linearization to produce recombinant adenoviral particles according to an embodiment of the invention.

Figure 16:
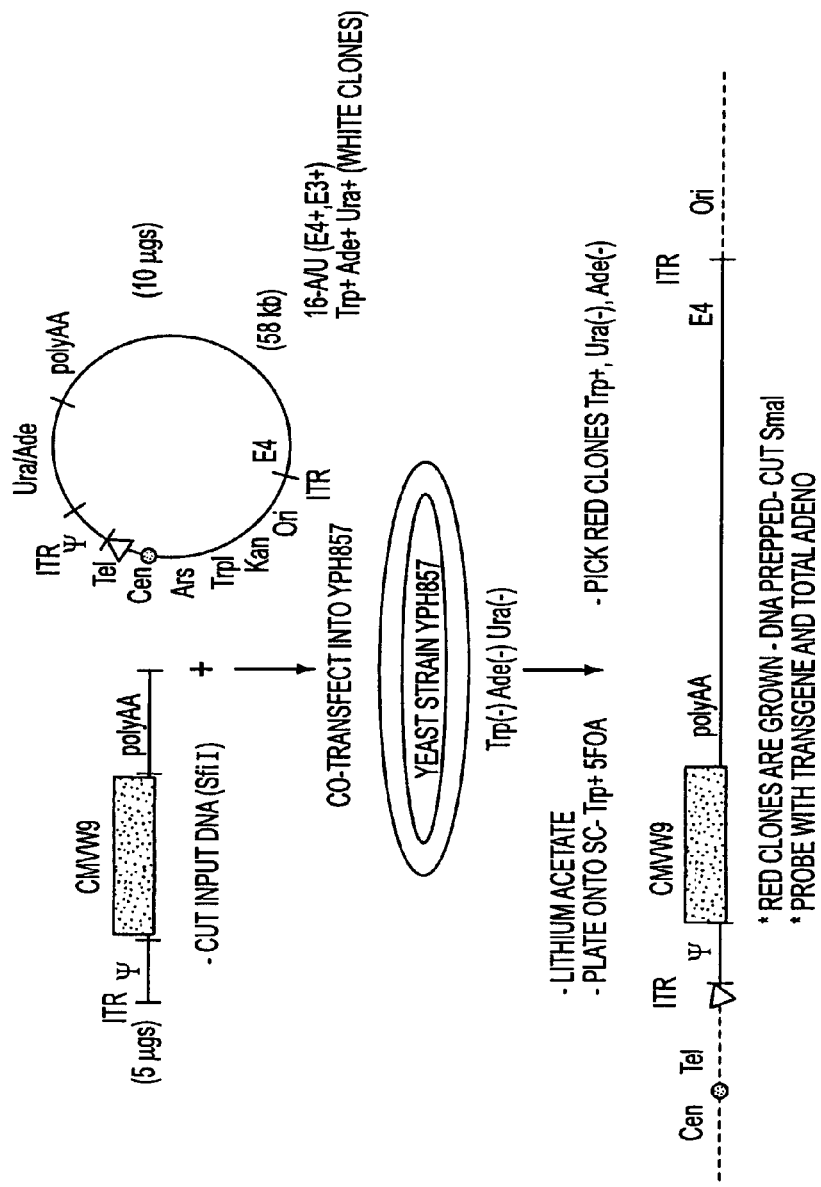

FIG. 16 is a diagrammatic representation showing moving a transgene (CMV-W9) into the E1 region of an Ad5 vector.

DETAILED DESCRIPTION OF INVENTION

The invention relates to the manipulation and delivery of large nucleic acids. The invention further relates to recombinational cloning vectors and systems and to methods of using the same.

It was an unexpected discovery to learn that a versatile cloning system capable of functioning in widely unrelated cell types and cell cycle stages, thus providing powerful engineering tools and methods to combine the benefits of different systems, could be developed. The hybrid cloning systems and methods of the invention combine the high versatility of yeast as a system for the capture and manipulation of a given nucleic acid and the high efficiency of bacterial systems for the amplification of such nucleic acid. Recombinational vectors relying on homologous recombination to mediate the isolation, manipulation and delivery of large nucleic acid fragments were constructed. The invention described herein also provides methods for using such recombinational cloning vectors to clone, to manipulate and to deliver large nucleic acids. Finally, the invention provides methods for using such recombinational cloning systems as potentiators of transgenic plant and animal studies and for gene therapy approaches, and for plant as well as animal genetic engineering approaches.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of yeast genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

In the description that follows, a number of commonly used terms used in recombinant DNA (rDNA) technology are utilized.

An "isolated nucleic acid molecule", "isolated nucleic acid" or an "isolated nucleic acid sequence", as is generally understood and used herein, refers to a polymer of nucleotides and includes but should not be limited to deoxyribonucleic acid (DNA) and ribonucleic acid (RNA).

A "recombinant DNA" is any DNA molecule formed by joining DNA segments, including from different sources, using recombinant DNA technology (i.e., molecular genetic engineering).

A "DNA segment", as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

A "gene" is a DNA encoding a single polypeptide chain or protein, and as used herein may include the 5' and 3' untranslated ends. The polypeptide can be encoded by a full-length sequence or any portion of the coding sequence, so long as the functional activity of the protein is retained.

"Complementary DNA (cDNA)" is a recombinant nucleic acid molecule synthesized by reverse transcription of messenger RNA ("mRNA").

A "structural gene" is a DNA that is transcribed into mRNA, which then is translated into a polymer of amino acids characteristic of a specific polypeptide.

A "restriction endonuclease" (also a "restriction enzyme") is an enzyme that has the capacity to recognize a specific sequence of bases (usually 4, 5 or 6 base pairs in length) in a nucleic acid molecule, and to cleave the nucleic acid at or near the site. For example, EcoRI recognizes the sequence GAATTC/CTTAAG.

A "rare restriction endonuclease recognition site" is one which does not occur frequently in the nucleic acid. Non-limiting examples of rare restriction endonuclease recognition sites include nucleic acids recognized by the enzymes I-SceI and NotI. Whereas restriction endonucleases that recognize sequences that are common in the genome yield "smears" when genomic DNA is digested with same and displayed by size by agarose gel electrophoresis and staining with ethidium bromide because a wide range of DNA fragments results, a rare cutter, because the recognition sites are not common in the genome, would under the same conditions yield discrete bands of DNA fragments.

A "restriction fragment" is a DNA molecule produced by digestion with a restriction endonuclease. A given genome or nucleic acid can be digested by a particular restriction endonuclease into a set of restriction fragments.

The Southern hybridization procedure is a means to visualize a particular DNA. A labeled DNA molecule or "probe" is hybridized to the fractionated, single-stranded DNA bound to a solid substrate, such as a nitrocellulose filter. The areas on the filter that carry DNA complementary to the labeled DNA probe become labeled themselves as a consequence of the reannealing reaction. The areas of the filter that exhibit such labeling are visualized. The hybridization probe generally is produced by molecular cloning of a specific DNA fragment.

An "oligonucleotide", "oligo" or "oligomer" is a molecule comprised of two or more deoxyribonucleotides or ribonucleotides. The exact size will depend on many factors which, in turn, depends on the ultimate function or use of the oligonucleotide. An oligonucleotide can be derived synthetically or by cloning.

A "primer" is an oligonucleotide which is capable of annealing near or at a target. The primer generally is a single-stranded nucleic acid and often serves as an initiation point for DNA synthesis when placed under conditions in which synthesis of a primer extension product, which is complementary to a nucleic acid strand, is initiated.

"Expression" is the process by which a structural gene produces a polypeptide. It involves transcription of the gene into mRNA and may also include the translation of such mRNA into a polypeptide.

A "vector" is a vehicle for carrying a nucleic acid. A vector is a nucleic acid carrier in which a nucleic acid of interest is inserted therein as an integral part of the vehicle nucleic acid. A vector often includes beneficial nucleic acids that serve a particular function, for example, a multiple cloning site, origin of replication site, selectable markers and so on.

A "cloning vector" is a nucleic acid that is suitable for carrying nucleic acids of interest contained therein as part of a single molecule. The cloning vector can serve to capture a nucleic acid of interest for further manipulation and amplification.

An "expression vector" is a vector or vehicle similar to a cloning vector but which is capable of expressing a nucleic acid that has been cloned therein, after transformation into a host. The cloned nucleic acid usually is placed under the control of (i.e., operably linked to) certain control or regulatory nucleic acids such as promoter sequences. Expression control sequences will vary depending on the conditions under which expression is to occur, for example, whether the vector is designed to express the operably linked gene in a prokaryotic or eukaryotic host. The vector additionally can contain transcription elements such as enhancer elements, termination sequences and tissue-specificity elements, as well as translational initiation sites and translational termination sites.

A "functional derivative" of a sequence, either protein or nucleic acid, is a molecule that possesses a biological activity (either functional or structural) that is substantially similar to a biological activity of the parent protein or nucleic acid from which the derivative is made. A functional derivative of a protein can contain post-translational modifications such as covalently linked carbohydrate, depending on the necessity of such modifications for the performance of a specific function. The term "functional derivative" is intended to include the "fragments", "segments", "variants", "analogs" or "chemical derivatives" of a molecule.

As used herein, a molecule is said to be a "chemical derivative" of another molecule when additional chemical moieties not normally a part of the molecule are included. Such moieties, for example, can improve the solubility, absorption, biological half life and the like of a molecule. The moieties alternatively can decrease the toxicity of the molecule, eliminate or attenuate any undesirable side effect of the molecule and the like. Moieties capable of mediating such effects are disclosed in "Remington's Pharmaceutical Sciences" (1980). Procedures for coupling such moieties to a molecule are well known in the art.

A "variant" of a protein or nucleic acid is meant to refer to a molecule substantially similar in structure and biological activity to either the parent protein or nucleic acid. Thus, provided that the two molecules possess a common activity and can substitute for each other, the two are considered variants, as that term is used herein, even if the composition or secondary, tertiary, or quaternary structure of one of the molecules is not identical to that found in the other, or if the amino acid or nucleotide sequence is not identical.

A "mutation" is any detectable change in the genetic material, which can be transmitted to daughter cells, and possibly even to succeeding generations giving rise to mutant cells or mutant individuals. If the descendants of a mutant cell give rise only to somatic cells in multicellular organisms, a mutant spot or area of cells arises in a solid culture. Mutations in the germ line of sexually reproducing organisms can be transmitted by the gametes to the next generation resulting in an individual with the new mutant condition perhaps in both somatic and germ cells. A mutation can be any (or a combination of) detectable, unnatural change affecting the chemical or physical constitution, mutability, replication, phenotypic function or recombination of one or more deoxyribonucleotides; nucleotides can be added, deleted, substituted for, inverted or transposed to new positions with and without inversion. Mutations can occur spontaneously and can be induced experimentally by application of mutagens. A mutant variation of a nucleic acid molecule results from a mutation. A mutant polypeptide can result from a mutant nucleic acid molecule.

A "polylinker" is a constructed DNA that will introduce restriction recognition sites, which may be used to map and to clone, into a known vector or plasmid. A polylinker is also identified as a "multiple cloning site".

A "purified" protein or nucleic acid is a protein or nucleic acid that has been separated from a cellular component. Purified proteins or nucleic acids have been isolated to a level of purity not found in nature. "Isolated" is meant to indicate some level of purification not found in nature.

The instant invention provides a novel cloning system which includes (a) a first arm in turn containing a first selectable marker and a first cyclization element; and (b) a second arm containing a second selectable marker and a second cyclization element. One of the arms may also include an origin of replication.

The term "arm" as used herein denotes one of the two arms, also designated as first and second arms or left and right arms, necessary to produce a moiety capable of replication in a yeast host and a bacterial host. The arms according to the invention preferably assemble in yeast. That enables genetic manipulation to be effected in the highly versatile yeast system. Yeast vectors have been described extensively in the literature and methods of manipulating the same also are well known as discussed hereinafter (see e.g., Ketner et al. (1994) Proc. Natl. Acad. Sci. (USA) 91:6186–6190).

Following genetic manipulation, the cloning system allows the transition to a bacterial environment, suitable for the preparation of larger quantities of nucleic acids. Representative examples of a bacterial type vector include the P1 artificial chromosome, bacterial artificial chromosome (BAC) and single copy plasmid F factors (Shizuya et al. (1992) Proc. Natl. Acad. Sci. 89:8794–8797). Similarly, bacterial vectors are well known in the art (e.g., Ioannou et al. (1994) Nature 6:84–89).

The invention also provides a recombinational vector comprising a yeast selectable marker; a bacterial selectable marker; a telomere; a centromere a yeast origin of replication; a bacterial origin of replication; and a rare restriction endonuclease recognition site in a single molecule, such as a plasmid or episome.

The recombinational vector of interest enables homologous recombination in yeast to capture and to integrate in a vector of interest a target nucleic acid of interest. The target nucleic acid of interest can be a large nucleic acid, and can include, for example, a vector, such as a viral vector, including the foreign gene of interest contained therein. The foreign gene of interest in the viral vector is one in which the transcribed product thereof, and perhaps the translation product of the transcription product, often has a benefit in a host of interest, such as a human. Thus, the invention of interest enables cloning and preparation of viral vectors containing a therapeutic gene of interest.

The vectors according to the invention comprise an appropriately oriented DNA that functions as a telomere in yeast and a centromere. Any suitable telomere may be used. Suitable telomeres include without limitation telomeric repeats from many organisms, which can provide telomeric function in yeast. The terminal repeat sequence in humans $(TTAGGG)_N$, is identical to that in trypanosomes and similar to that in yeast $((TG)_{1-3})_N$ and Tetrahymena $(TTGGG)_N$ (Szostak & Blackburn (1982) Cell 29:245–255; Brown (1988) EMBO J. 7:2377–2385; and Moyzis et al. (1988) Proc. Natl. Acad. Sci. 85:6622–6626).

The term "centromere" is used herein to identify a nucleic acid, which mediates the stable replication and precise partitioning of the vectors of the invention at meiosis and at mitosis thereby ensuring proper segregation into daughter cells. Suitable centromeres include without limitation the yeast centromere, CEW4, which confers mitotic and meiotic stability on large linear plasmids (Murray & Szostak (1983) *Nature* 305:189–193; Carbon (1984) *Cell* 37:351–353; and Clark et al. (1990) *Nature* 287:504–509)).

At least one of the two arms or the circular vector according to the invention includes at least one replication system that is functional in a host cell/particle of choice. As it will become apparent hereinafter, one of skill will realize that the manipulation, amplification and/or delivery of a target nucleic acid of choice may entail the use of more than one host cell/particle. Accordingly, more than one replication system functional in each host cell/particle of choice may be included.

Where one of the host cells is a mammalian host cell, replication system(s) include those derived from viruses known to replicate in mammalian cells such as, for example, SV40, Epstein-Barr, retrovirus, papova virus, adenovirus, papilloma virus, adeno-associated virus (AAV), lentivirus, hcMV and the like. When a host cell(s) is a prokaryote, particularly *E. coli*, replication system(s) include those which are functional in prokaryotes, such as, for example, P1 plasmid replicon, ori, P1 lytic replicon, ColE1, BAC, single copy plasmid F factors and the like.

In preferred embodiments of the invention, either one or both arms and the circular vector further include a yeast origin of replication capable of supporting the replication of large nucleic acids. Preferred non-limiting examples of replication regions according to the invention include the autonomously replicating sequence or "ARS element." ARS elements were identified as yeast sequences that conferred high-frequency transformation. Tetrahymena DNA termini have been used as ARS elements in yeast along with ARS1 and ARSH4 (Kiss et al. (1981) *Mol. Cell Biol.* 1:535–543; Stinchcomb et al. (1979) *Nature* 282:39; and Barton & Smith (1986) *Mol. Cell Biol.* 6:2354). In preferred embodiments of the invention, for each pair of arms (left and right arms) there may be two or more origins of replication. The latter has been found to be a preferable embodiment for vectors in which very long DNA sequences are introduced.

The first and/or the second arm according to an aspect of the invention may be joined in a circularized vector form (e.g., plasmid form). Circularization can occur in vivo or in vitro using the arm of interest. Alternatively, a circular vector of interest can be used. As used herein and explained in part, in brief hereinabove, the term "vector" designates a plasmid or phage DNA or other nucleic acid into which DNA or other nucleic acid may be cloned. The vector may replicate autonomously in a host cell and may be characterized further by one or a small number of restriction endonuclease recognition sites at which such nucleic acids may be cut in a determinable fashion and into which nucleic acid fragments may be inserted. The vector further may contain a selectable marker suitable for the identification of cells transformed with the vector.

The term "selectable marker" is used herein to identify a sequence that allows the detection and/or selection of recombinant host cells containing a vector by negative and/or positive methodologies. Such selectable negative or positive marker may be an inserted gene or nucleic acid. One of skill in the art will appreciate that the choice of a suitable selectable marker depends on the genotype of the host cell, virus or other entity used. Thus, the selection of arms and vectors in bacteria (described in more detail infra) may be achieved by the use of bacterial selectable markers. Preferred non-limiting examples of bacterial selectable markers include, for example, genes that render a cell sensitive or resistant to a factor that can have a telling impact on that cell, such as being cytotoxic to that cell. Thus, known selection genes include those that impart resistance to various antibiotics, such as the AMP (ampicillin), TET (tetracycline) and KAN (kanamycin) markers.

Similarly, the selection of vectors in yeast may be accomplished by the use of yeast selectable markers. Examples include the known HIS3, TRP1, URA3, LEU2 and ADE markers. In some embodiments of the invention, a vector or arm may comprise two or more selectable markers. Thus, in one embodiment, an arm may comprise an ADE marker to be lost on homologous recombination with the target nucleic acid, and a HIS3 marker. The other arm may comprise a TRPI marker. Selection is achieved by growing transformed cells on the suitable drop-out selection media (see e.g., Watson et al. (1992) *Recombinant DNA*, $2^{nd}$ ed., Freeman and Co., New York, N.Y.). For example, HIS3 allows the selection of cells containing the first arm. TRP1 allows the selection of cells containing the second arm. ADE allows screening and selection of clones in which homologous recombination took place. ADE enables color selection (red).

The term "cyclization element" is used to denote a nucleic acid capable of promoting the circularization of the arms of interest into a recombinant vector. One of skill will appreciate that suitable cyclization elements include a variety of known repetitive sequences that promote recombinational events. Hence, representative examples of cyclization elements include tandem repeats, such as, for example Alu sequences (Garza et al. (1989) *Science* 246:641–646). Another cyclization element involves the interaction between LoxP sites, which on contact with Cre recombinase, produce a site-specific recombination event at a predetermined site. Nonlimiting representative examples of Lox sites suitable as cyclization elements are described in U.S. Pat. No. 5,658,772. In another embodiment, the cyclization elements are amenable to FLP-mediated recombination. Nonlimiting representative examples of FLP sequences and of FLP recombinase suitable as cyclization elements according to the invention are described in U.S. Pat. No. 5,677,177.

To facilitate cloning, each arm also should include a rare restriction endonuclease recognition site. A "rare restriction endonuclease recognition site" is a substrate for a restriction endonuclease enzyme that does not occur frequently in the nucleic acid. Non-limiting examples of rare restriction endonuclease recognition sites include those recognized by I-SceI and NotI.

In yet another preferred embodiment of the invention, each arm contains a polylinker.

In addition, the invention provides a cloning system in which both arms or the circular vector also includes nucleic acids homologous to the 5' and to the 3' terminus sequence of a target nucleic acid of interest.

The term "homologous" as used herein means being of sufficient linear identity or similarity to have the ability to hybridize to a portion of a target nucleic acid made or which is single-stranded, such as a gene, a transcriptional control element or intragenic DNA. Such hybridization is ordinarily the result of base-specific hydrogen bonding between complementary strands, preferably to form Watson-Crick base pairs. As a practical matter, such homology can be inferred from the observation of a homologous recombination event. Preferably, such homology is from about 8 to about 1000 bases of the linear nucleic acid, and most preferably from about 12 to about 500 bases. One skilled in the art will appreciate that homology may extend over longer stretches of nucleic acids.

"Target sequence", "foreign gene of interest", transgene" and "insert" are used to refer to any sequence or nucleic acid sought to be inserted in the cloning and expression system or vector according to the invention.

Target nucleic acids of the invention may vary considerably in complexity. The target nucleic acid may include viral, prokaryotic or eukaryotic DNA, more specifically, mammalian DNA, such as cDNA, more specifically both exonic (coding) as well as intronic (noncoding) sequences. Hence, the target nucleic acid of the invention may include one or more genes. In a preferred embodiment, the target nucleic acid is a chromosome. The target nucleic acid also may be of any origin and/or nature. Thus, the target nucleic may be a prokaryotic or a eukaryotic nucleic acid. The target nucleic acid also may be a virus, including a DNA virus, such as, for example, adenovirus, human herpes virus, varicella zoster virus, pox virus, papovavirus, cytomegalovirus (CMV), Epstein-Barr virus, adeno-associated virus (AAV) or Herpes simplex virus—or an RNA virus, such as a retrovirus, a lentivirus, e.g., human immunodeficiency virus, murine leukemia virus or alphavirus.

The vectors of the invention may be modified further to include functional entities other than the target sequence which may find use in the preparation of the construct(s), amplification, transformation or transfection of a host cell, and—if applicable—for integration in a host cell.

In an embodiment of the invention, the target nucleic acid includes a regulatory nucleic acid. A "regulatory sequence" or "regulatory nucleic acid" is used herein in a broad sense to designate any sequence or a nucleic acid which modulates (either directly or indirectly, and either up or down) the replication, transcription and/or expression of a nucleic acid controlled thereby. Control by such regulatory nucleic acid may make a nucleic acid constitutively or inducibly transcribed and/or translated. Examples of regulatory nucleic acids include without limitation transcriptional promoters and enhancers. Thus, the arms and vector of the invention may include a transcriptional regulatory region such as, for example, a transcriptional initiation region. One skilled in the art will appreciate that a plethora of transcriptional initiation sequences have been isolated and are available, including thymidine kinase promoters, β-actin promoters, immunoglobin promoters, methallothionein promoters, human cytomegalovirus promoters and SV40 promoters.

The invention also provides a method of producing a gap-filled vector. A vector is defined as being "gap-filled" on homologous recombination and insertion of a target nucleic acid according to the invention by filling in the region (gap) between the sequences homologous to the 5' and the 3' regions of the target nucleic acid. Hence, one would contact the instant cloning system with a target nucleic acid under conditions that allow homologous recombination. In a preferred embodiment, the method combines: (i) a first arm including a first nucleic acid homologous to the 5' terminus of a target nucleic acid, a first selectable marker and a first cyclization element; (ii) a target nucleic acid; and (iii) a second arm including a second nucleic acid homologous to the 3' terminus of a target nucleic acid, a second selectable marker and a second cyclization element, under conditions which allow homologous recombination. The method according to that aspect of the invention produces a gap-filled vector by homologous recombination between the two arms and the target nucleic acid. The exchange between the homologous regions found in the arms and the target nucleic acid is effected by homologous recombination at any point between the homologous nucleic acids.

With respect to a circular vector of interest, the "gap filling" essentially is insertion, that is, subcloning, of the target sequence into the vector.

In a preferred embodiment, homologous recombination may be effected in vitro according to methodologies well known in the art. For example, the method of the invention can be practiced using yeast lysate preparations. In another preferred embodiment, homologous recombination takes place in vivo. Hence, the method of the invention may be practiced using any host cell capable of supporting homologous recombination events such as, for example, bacteria, yeast and mammalian cells. One skilled in the art will appreciate that the choice of a suitable host depends on the particular combination of selectable markers used in the cloning system of the method.

Techniques that may be used to introduce the vector into a host cell of interest include calcium phosphate/DNA coprecipitation, electroporation, bacterial-protoplast fusion, microinjection of DNA into the nucleus and so on. The DNA may be single stranded or double stranded, linear or circular, relaxed or supercoiled. One of skill will appreciate that a number of protocols may be used virtually interchangeably to transfect mammalian cells as set forth for example in Keown et al. (*Meth. Enzymol.* 185:527–537, 1990). Preferably, eukaryotic cells are used, such as a yeast cell, such as *Saccharomyces cerevisiae, S. pombe* or *S. ustillago*. Methods for introducing nucleic acids in a yeast cell are well known in the art. Hence, such a step may be accomplished by conventional transformation methodologies. Non-limiting examples of suitable methodologies include electroporation, alkali cations protocols and transformation of spheroplast cells.

Recombinant yeast cells may be selected using the selectable markers described herein according to methods well known in the field. Hence, one skilled in the art will appreciate that recombinant yeast cells harboring a gap-filled vector of the invention may be selected on the basis of the selectable markers included therein. Hence, recombinant vectors carrying HIS3 and TRPI may be selected by growing transformed yeast cells in the presence of drop-out selection media lacking his and trp. Isolated positive clones may be purified further and analyzed to ascertain the presence and structure of the recombinant vector of the invention by, e.g., restriction analysis, electrophoresis, Southern blot analysis, polymerase chain reaction or the like.

The invention further provides gap-filled vectors engineered according to the method of the invention. Such a vector is the product of homologous recombination between the arms or vector of the invention and a target nucleic acid of choice.

The invention also provides a prokaryotic cell and a eukaryotic host cell harboring the cloning system or vector according to the invention. In one embodiment, the eukaryotic host cell is a yeast cell. In a preferred embodiment of the invention, the yeast cell is *Saccharomyces cerevisiae, S. pombe* or *S. ustillago*. A suitable bacterial cell is *E. coli* and *B. subtilis*.

In another aspect, the invention provides a method of circularizing the gap-filled arms of the invention. The gap-filled vector may be circularized by contacting the first and the second Lox sites contained therein with Cre, thereby producing a circularized gap-filled vector by site-specific recombination. The gap-filled vector may be circularized in bacteria. The invention further provides a bacterial cell comprising the circularized gap-filled vector of the invention.

The invention further provides methods for cloning, manipulating and delivering a large target nucleic acid to a cell or particle, such as, for example, a virus. According to the invention, the viral cloning system is engineered to contain a target sequence and is maintained as a non-infectious derivatized clone in which it is possible to use the high homologous recombination rate of yeast to modify genetically any nucleic acid within the cloned target nucleic acid with great efficiency as it will become apparent from the examples provided hereinafter.

The gap-filled linear vector may be converted to a circular vector in vitro or in vivo, for example, in a bacterium. The circular vectors of interest can be amplified, purified, cut and used to recover sufficient amounts of DNA to be introduced either directly into a cell or into a suitable delivery system for subsequent delivery to a target cell. The methodology offers great versatility to clone and to modify any large viral or non-viral genome, and easily facilitate the use thereof as recombinational vectors.

Direct delivery of a gap-filled vector into a cell may be effected by methods well known in the field such as, for example, calcium phosphate transformation methodologies or electroporation (see Sambrook et al., supra).

Accordingly, the invention provides a method for producing a recombinant delivery unit including the steps of: (a) producing a gap-filled vector containing a target sequence; (b) optionally circularizing the gap-filled vector arms of the invention; (c) propagating the vector; and (d) introducing the gap-filled vector in a delivery unit. In one embodiment of the invention, the delivery unit is a virus. Hence, introduction of the gap-filled vector is effected by introducing the vector in a complementing mammalian cell to generate a replication deficient viral vector. It will be appreciated that a gap-filled vector can be circularized or linearized before being amplified and being placed in a delivery unit.

Thus, the invention also provides a method of producing a recombinant delivery unit comprising the steps of: (a) producing a gap-filled vector containing a target sequence; (b) optionally circularizing the gap-filled vector arms; (c) propagating the vector; (d) linearizing the gap-filled vector; and (e) introducing the gap-filled vector in a delivery unit. In one embodiment of the invention, the delivery unit is a virus. Hence, introduction of the linearized gap-filled vector is effected by introducing the vector in a complementing mammalian cell to generate a replication deficient viral vector. One of skill will appreciate that whether the vector is linearized is a function of the sequence being manipulated.

The term "delivery unit" means any entity that is capable of associating with the gap-filled vectors (DNA or RNA) of the invention, and that is capable of mediating the transport of such vector DNA or RNA to a particular organ, tissue or to individual cell type, in vivo or ex vivo. Delivery units are known in the art and include liposomes, protein complexes, polysaccharides, synthetic organic polymers or amphiphiles (including lipids) that are capable of complexing to DNA. Methods for introducing the vectors of the invention in a delivery unit are well known in the art, see, e.g., Sambrook et al., supra. It will be apparent to one of skill that such methods vary considerably depending on the nature of the delivery unit used and of the target nucleic acids.

As discussed hereinabove, the target nucleic acid may be DNA of various types (e.g., animal, plant, or viral in origin). Thus, the insertion of the gap-filled vector nucleic acid in a delivery unit depends on the nature of the target nucleic acid and the delivery unit cell or particle of choice in any given application. As discussed elsewhere herein the target nucleic acid in the gap-filled vector may include viral nucleic acids alone or in combination with nucleic acids to be expressed in a host cell or in the particle of choice. Target nucleic acids including viral nucleic acids may be introduced in a viral particle by transformation methodologies. One of skill will appreciate that several methods are available and well known in the field. One such methodology includes the transfection of nucleic acids coding for viral proteins in packaging cell lines providing complementing packaging factors for the packaging of viral particles. In those instances, the target nucleic acids are introduced in the viral capsid, for example, by packaging, using the appropriate complementing cell line.

The gap-filled vectors including target nucleic acids enables coding and manipulation of large nucleic acids, such as recombinant adenoviral vectors. For example, gap-filled arms are circularized (e.g., by Lox/Cre mediated recombination as described supra), amplified and linearized using a rare cutting restriction endonuclease engineered for the purpose. The linearized vector then is used to transfect a complementing packaging cell line enabling the production of missing viral functions and thereby producing fully assembled adenovirions. Examples of packaging cell lines useful for the packaging of adenoviral sequences include 293 cells, 293E4 cells, (Wang et al. (1995) *Gene Therapy* 2:775–785) and 911 cells (Fallaux et al. (1996) *Human Gene Therapy* 7:215–222). Such virions may be used further for gene therapy applications as described below. One of skill in the art will appreciate that the vectors and methods described herein may be modified easily to engineer a variety of viral vectors to be packaged for delivery according to standard methods known in the field.

In another embodiment of the invention, the gap-filled vector of the invention is introduced either in a closed circular form or in a linearized form in a non-viral delivery unit. Examples of non-viral delivery units include liposomes, protein complexes, polysaccharides, synthetic organic polymers and amphiphiles (including lipids) capable of complexing to DNA. Methods for introducing DNA into such delivery units are well known in the art, see, for example, "Gene Therapy Protocols", Robbins ed., Humana Press, Totowa, N.J. (1997) and "Gene Therapy", Lemoine & Cooper, eds., Bios Scientific Publishers, Oxford, U.K. (1997). Hence, for example, vectors of the invention may be introduced using calcium phosphate methodologies, electroporation or microinjection.

The cloning systems and methods of the invention are useful for a variety of purposes. For example, the vectors can be used for therapeutic or diagnostic purposes including gene transfer in vitro and in vivo, vaccination in vivo and gene therapy. Assembled delivery units of the invention may be used to deliver the nucleic acid cargo contained therein to a target cell.

Hence, the invention may be used to provide a missing gene function and thus ameliorate disease symptoms. For example, the diseases beta thalassemia and sickle cell anemia are caused by aberrant expression of the adult beta globin gene. Most individuals suffering from those diseases have normal copies of the fetal gene for beta globin. However, the fetal gene is hypermethylated and is silent. Replacement of the fetal globin gene could provide the needed globin function, thereby ameliorating the disease symptoms.

The invention also could be used to up-regulate or down-regulate a gene to compensate for aberrant gene expression patterns responsible for human diseases. In addition, the cloning systems and the methods of using the same are useful in therapeutic approaches to benign and malignant tumors and other human diseases involving suppression of gene expression. In other preferred embodiments, the vectors and methods of the invention are used for viral, plant, as well as animal, molecular genetic engineering.

Thus the invention of interest essentially provides for a means to produce large amounts of, in particular, large nucleic acids, such as recombinant vectors carrying a gene of interest, such as a therapeutic gene of interest, wherein the products of the instant invention can be used for any of a variety of uses as known for recombinant gene and gene products, such as therapeutic or diagnostic uses.

The following examples are intended to illustrate further certain preferred embodiments of the invention and are not limiting in nature. Those skilled in the art will recognize, or be able to ascertain, using no more than routine experimentation, numerous equivalents to the specific substances and procedures described herein. Such equivalents are considered to be within the scope of this invention, and are covered by the following claims.

EXAMPLES

The following is a list of materials and methods used in the examples described herein.

Plasmids: The gap-filling vectors p-left, pTrp 34.1, PHisAdv-22, pTrp 1014-29 and pTrp 366-22 are described in the Figures. The vectors contain all of the cis-acting elements required to gap-fill, maintain and circularize a vector according to the invention in both yeast and bacteria. Vector p2Puc is described in the Figures. That is an example of a vector that can be used to shuttle transgenes into various regions of an adenovirus vector.

pAd10sac BII, used for the construction of pED-R2P2, is described in Pierce et al. (*Proc. Natl. Acad. Sci.* (USA) 89:2056–2060, 1992); and pYAC-S/N-3 used for the construction of pED-R2P2 is derived from pYAC4, by the insertion of a linker at the EcoRI site and the introduction of NotI and SfiI sites. pYAC4 is described in Burke et al., *Science* 236:806–812 (1987). Ad5-1014 used for the construction of pTrp1014-29 was isolated by PCR amplification of the A1014 adenovirus as described in Wang et al., Gene Therapy 4:393–400 (1997). The pAdLOX used to construct pLOX-Ade/Ura and pLOX-CMV-W9 is described in Hardy et al. (1997) *J. Virol.* 71:1842–1849).

Yeast and Bacteria Strains: *Saccharomyces cerevisiae* strain YPH857 (MATα, his3-Δ200, trp 1Δ1, ura3-52, leu2-Δ1, Lys 2-801, ade2-101) was used in the yeast transformations and allowed selection for Trp$^+$ and HIS$^+$ vectors. *E. coli* strain N53529, which contains a constitutively expressed P1 Cre recombinant gene (as described, for example, in Sauer et al. (1988) *Gene* 70:331–341; and Sauer et al. (1989) *Nucl. Acids Res.* 17:147–161), was used to circularize the gap-filled arms of the invention by using Lox/Cre recombination as described for example in Sauer et al. (1988) supra; Sauer et al. (1989) supra; Abremski et al. (1983) *Cell* 32:1301–1311; and Steinberg et al (1983) *Ann. Rev. Genet.* 17:123–154.

The DH10B strain (Life Technologies) was made electrocompetent by growth to an $OD_{550}$ of 0.7, collecting and washing the same with ice-cold 10% glycerol, flash freezing in a dry-ice ethanol bath and storing at −80° C. Total yeast DNA was prepared as described in Sherman et al., infra, and electroporated in *E. coli* strain DH10B by using 0.1 cm cuvettes at 1,800 V, 200 ohms, and 25 mF in a Bio-Rad Gene Pulsar Electroporator. Cells were allowed to recover and clones were selected on kanamycin (5 mg/l) plates. One of skill in the art will appreciate that many other transformation methods known in the art may be substituted in lieu of the ones specifically described or referenced herein.

The 1014 deletion is described in Armentano et al., *Hum. Gen. Ther.* 6:1343–1353 (1995). The 366 deletion is described in Armentano et al., *J. Virol.* 71:2408–2416 (1997).

Agarose Gel Electrophoresis. To determine the length of restriction fragments, an analytical method for fractionating double-stranded DNA molecules on the basis of size is required. The most commonly used technique (though not the only one) for achieving such a fractionation is agarose gel electrophoresis. The principle of the method is that DNA molecules migrate through a sieving gel that retards the movement of the largest molecules to the greatest extent and the movement of the smallest molecules to the least extent. Pulsed field gel electrophoresis (PFGE) allows the fractionation of larger DNA fragments.

Southern Transfer Procedure. The purpose of the Southern transfer procedure (also referred to as Southern blotting) is to transfer DNA fractionated by agarose gel electrophoresis onto a nitrocellulose filter paper or another appropriate surface or support, while retaining the relative positions of DNA fragments resulting from the fractionation procedure. The methodology used to accomplish the transfer from agarose gel to nitrocellulose involves drawing the DNA from the gel into the nitrocellulose paper by capillary action or electrophoretic transfer. Probing of blotted nucleic acids immobilized on a nitrocellulose filter as by the Southern hybridization transfer procedures may be accomplished by using labeled probes.

Nucleic Acid Hybridization. Nucleic acid hybridization depends on the principle that two single-stranded nucleic acid molecules that have complementary base sequences will reform the thermodynamically favored double-stranded structure under the proper conditions. The double-stranded structure will be formed between two complementary single-stranded nucleic acids even if one is immobilized on a nitrocellulose filter as by the Southern hybridization transfer procedure. DNA to be tested is digested with a restriction endonuclease, fractionated by agarose gel electrophoresis, converted to the single-stranded form and transferred to nitrocellulose paper. The bound nucleic acid was available for reannealing to the hybridization probe. Examples of hybridization conditions can be found in Ausubel et al., "Current Protocols in Molecular Biology", John Wiley & Sons, Inc., New York, N.Y. (1989). For example, a nitrocellulose filter is incubated overnight at 68° C. with labeled probe in a solution containing 50% formamide, high salt (either 5×SSC [20×: 3 M NaCl/0.3 M trisodium citrate] or 5× SSPE [20×: 3.6 M NaCl/0.2 M $NaH_2PO_4$/0.02 M EDTA, pH 7.7]), 5× Denhardt's solution, 1% SDS and 100 μg/ml denatured salmon sperm DNA. That is followed by several washes in 0.2× SSC/0.1% SDS at a temperature selected based on the desired stringency: room temperature (low stringency), 42° C. (moderate stringency) or 68° C. (high stringency). The temperature selected is determined based on the melting temperature ($T_m$) of the DNA hybrid. Other hybridization and washing conditions can be employed at the discretion of the artisan and governed by the physical characteristics of the nucleic acids, nucleic acid hybridization kinetics and the desired outcome, as known in the art.

Hybridization Probe. To visualize a particular DNA sequence in the Southern hybridization procedure, a labeled DNA molecule or hybridization probe is reacted to fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe generally is produced by molecular cloning of a specific DNA. The label is as known in the art, such as a radionuclide, light emitting moiety, enzyme, antigen and so on.

PCR Amplification. The Polymerase Chain Reaction (PCR) is a well known method for generating large amounts of a target sequence. In general, amplification primers are annealed to a target substrate nucleic acid sequence. Using appropriate enzymes, and in the appropriate conditions, sequences found adjacent to, or in between the primers are amplified by synthesis. Sample PCR reaction conditions are dNTP's (final concentration 200 mM each deoxynucleotide tri-phosphate), 5' primer and 3' primer (600 mM each), template DNA (1 g), $MgSO_4$ (20 mM), DNA polymerase (2.5 U) in standard PCR reaction buffer (all concentrations given are final concentrations for the reaction). The reactions are carried out first at 94° C. for 3 minutes, then for 5 cycles of 94° C. for 1 minute, 55° C. for 1 minute and 68° C. for 3 minutes, followed by 15 cycles of 94° C. for 1 minute, 63° C. for 1 minute and 68° C. for 3 minutes, followed by holding the reaction at 4° C. Individual reaction conditions are configurable by the artisan, based on, for example, the desired outcome and the physical properties of the nucleic acids.

Example 1

Yeast and Bacteria Transformation

Yeast strain YPH857 was transformed with vector arms (PHis Adv-22 (5 µg); pTrp1014-29 (10 µg)) and Ad5 filler DNA (10 µg) by the lithium acetate method as described in Sheistl & Geitz (*Curr. Genet.* 16:339–346, 1989) and Sherman et al., "Laboratory Course Manual Methods in Yeast Genetics" (Cold Spring Harbor Laboratory Press, Cold Spring Harbor, 1986). Yeast transformants were selected on selective media lacking histidine and screened on selective media plates lacking tryptophan. Standard methods for yeast growth and phenotype testing were employed as described by Sherman et al., supra. *E. coli* strain N53529 or DH10B was made electrocompetent by growing the cells to an $OD_{550}$ of 0.7, then collected and washed twice with ice-cold 10% glycerol, flash frozen in a dry-ice ethanol bath and kept at −80° C. Total yeast DNA was prepared as described by Sherman et al., supra, and electroporated into *E. coli* by using, for example, a 0.1 cm cuvette at 1,800 V, 200 ohms and 25 mF in a Bio-Rad Gene Pulsar Electroporator. Cells were allowed to recover and clones were selected on kanamycin (5 mg/l) plates. One of skill will appreciate that many other transformation methods known in the art may be substituted in lieu of the ones specifically described or referenced herein.

Example 2

DNA Purification and Analysis

DNA from the vector was isolated and analyzed according to methods known in the art. For illustrative purposes, and without limiting the invention to the specific methods described, the DNA of a resultant representative vector gap-filled with adenoviral sequences (as described in the instant examples) was prepared in low-melting plugs and analyzed by pulse-field gel electrophoresis (PFGE), or digested with the appropriate restriction endonuclease (e.g., SmaI) and analyzed by conventional agarose gel electrophoresis. In the alternative, vectors were digested with two or more restriction endonucleases depending on the particular sequences cloned (e.g., SmaI, I-SceI and SmaI/I-SceI digestion and analysis on standard electrophoresis). Standard protocols useful for these purposes are fully described in Gemmill et al. (in "Advances in Genome Biology", Vol. 1, "Unfolding The Genome," pp 217–251, edited by Ram S. Verma). One of skill will appreciate that many other methods known in the art may be substituted in lieu of the ones specifically described or referenced.

Example 3

Construction of HIS Left Arm

A linker was cloned into pleft (Mendez et al. "Genome Mapping and Sequencing Meeting", Cold Spring Harbor Laboratory Press, Cold Spring Harbor, 1993) which included seven unique cloning sites, a Loxp site and a I-ScеI site (18mer rare cutter). The construct, pleft G-5, includes HIS3, telomere, LOXp site and the rare cutter site.

Example 4

Construction of TRP Right Arm

A linker was cloned into pAd10Sac BII (Pierce et al. (1992) *Proc. Natl. Acad. Sci.* (USA) 89:2056–2060) in which four unique sites and an I-SceI site (18mer rare cutter) were included. The next two fragments were derived from pYAC-s/n-3. The first fragment, which contains the CEN, TRP1 and ARS markers, was cut with AatII, blunt/filled with DNA polymerase Klenow (New England Biolabs, Beverly, Mass.) and then cut with SfiI to release the fragment. The second fragment which contains the TEL, was cut with XhoI; blunt/filled with DNA polymerase Klenow and cut with BamHI to release the fragment. A three-way ligation was set up with pAd10sacBII (SfiI/BamHI) and the previously described fragments. PTrp 34-1 has all the elements needed (TRP1, telomere, centromere, ARS and I-SceI site), P1 plasmid replicon, KAN, P1 lytic replicon (Pierce et al. (1992) *Proc. Natl. Acad. Sci.* 89:2056–2060), four unique cloning sites and a LoxP site, for a gap-filling arm. Trp 1014-29 and PTrp 366-22 were both created by PCR-based cloning of 1.5 kb of the 3' end of either AD5-1014 (Armentano et al. (1995) *Hum. Gene Ther.* 6:1343–1353) and/or AD5-366 (Armentano et al. (1997) *J. Virol.* 71:2408–2416), adding BamHI and I-SceI ends and cloning into PTrp 34-1 (I-SceI/BamHI). The clones can be used to gap-fill an insert containing an adenovirus vector and introduce either a 1014 E4 or 366 deletion, respectively. The vectors were linearized by BamHI for targeting.

Example 5

Gap-filling of Vectors

To illustrate the use of the cloning system according to the invention, representative arms pleft (left arm) and pTrp (right arm) were modified to contain sequences sharing 5' and 3' homology with a portion of the adenovirus genome (i.e., a representative target sequence). pleft 6 has a HIS3 yeast selectable marker, a yeast telomere sequence, LoxP site, I-Scel site and a polylinker in which 5' or 3' homology can be cloned. pTrp 34.1 has a TRPI yeast selectable marker, yeast telomere sequence, LoxP site, 1-Scel site, P1 plasmid replicon ori, P1 lytic replicon, KAN gene, ARS, CEN and a polylinker in which 5' or 3' homology can be cloned. The three elements were introduced in a YPH-857 yeast cell line by conventional methods.

Example 6

ΔE1/E4 (1014) Ad5 Construction

By using homologous recombination in yeast, the left arm, the right arm and the target sequences described supra using the overlapping homologous pieces are reconstructed into a single module in yeast. The construct is maintained and stable only if both arms, HIS3$^+$ (TEL) and TRP$^+$ (CEN, ARS, TEL), are present and functional. There are no limits to size or content of the filler DNA as long as a 5' end and a 3' end of homology can be cloned.

pTrp 1014-29 which contains sequences sharing sufficient 3' homology and the E4 deletion derived from Ad51014 was used with pHISADV-22, which contains the 5' end of homology and the E1 deletion derived from ADV-1. The two arms were co-transfected with Ad5 DNA into yeast (YPH857). Southern blot analysis of the resultant positive clones obtained by selection for His and screening for Trp by growth in the absence of tryptophan as described above, probed with total adenovirus DNA, identified a clone (YAC18 or Y18) found on further analysis to have all the markers (TRP$^+$, HIS$^+$). Y18 is about 65 kb in size. The analysis revealed that homologous recombination that generated YAC18 occurred at the 3' end of the E1Δ as compared to other clones that carried the Adenovirus, His and Trp markers but were larger by containing E1 due to homologous recombination occurring 5' of E1.

Example 7

Adeno Vector Construction

The representative vector, pED-R2P2, is useful to introduce the 1014 E4 deletion into the Ad5 virus. A 650 bp BclI fragment containing 0–1.3 mµ (map units, one map unit is about 360 bp; corresponding to the 5' end of Ad5) was isolated from pAdLOX by PCR amplification (using the same cycling parameters as described below) using a primer (5'-ATC GTG ATC ACA TCA TCA ATA ATA TAC C-3') (SEQ ID NO: 1) designed to hybridize to the LTR region, and another primer (5'-CAA GTA TCG GGT ATA TAC CTA CTA GTA CGT-3') (SEQ ID NO:2) designed to hybridize 650 bp from the 5' end of the Ad5 sequence. The primers were designed to generate a 650 bp fragment which would also contain flanking BclI sites (which are BamHI compatible). The resultant fragment was cloned in the BamHI site in pTrp 1014-29 which contains sequences sharing sufficient 3' end homology and the E4 deletion derived from Ad51014. The resulting 23 kb vector, pED-R2P2, was co-transfected with Ad5 DNA into yeast (YPH857), selected on Trp plates and screened for the presence of E3 sequences by Southern blot analysis. The gap-filled vector then were introduced into DH10B, kanamycin-selected and amplified. The resultant positive clones, obtained by selection for Trp, were probed with total adenovirus DNA to identify the clone designated as Adeno YAP-R2P2(1014), found on further analysis to have all the markers (i.e., GFP, and E3).

Example 8

Construction of a Mutant Adeno Vector

Mutations were introduced in Ad5 using the pED-R2D2 vector. The vector pED-R2D2 containing the 3' end homology and the E4 deletion Ad51014, together with the 5' end homology derived from the pED-R2D2 construct were co-transfected with either Ad5-GFP(E4+) DNA or with Ad5-GFP(366) DNA into yeast (YPH857) and selected on Trp plates. The gap-filled vectors then were introduced into DH 10B, kanamycin-selected and amplified. Analysis of clones, such as by restriction mapping, revealed the mutations expected.

Example 9

Modifications of the E1 Region of a Gap-Filled Adeno Vector pLOX-Ade/Ura was used to move yeast markers and the SV40 polyA sequences into the E1 region of an Adeno vector. pLOX-Ade/Ura was derived from pAdLOX to include the ADE2 yeast selectable marker, and a URA3 yeast selectable marker, TEL, LoxP site, I-ScelI site, 1 to 1.3 ml of Ad5 region (corresponding to the 5' region of Ad5) and a polylinker with SV40 polyA. pLOX-Ade/Ura was cut with Bsu36I, co-transfected with Ad5-GFP(E4+) DNA in yeast strain YPH857 and selected on SC-URA, SC-Trp plates. Ura/Trp positive clones were selected by virtue of being Ade positive and GFP negative. The clones then were moved from yeast into bacteria by electroporation. Once positive clones had been selected using kanamycin selection, the clones were amplified and purified by standard methodologies. The amplified DNA's then were digested with the requisite rare cutter to release the viral genome and used to transfect complementary cells and to rescue infectious adenoviruses.

pAdLOX was used to move a transgene (CMV-W9) into the E1 region of an Ad5 vector of the invention. The vector allows the introduction of a transgene into the Ad5 vector by using homologous recombination and the negative selection of 5FOA of the URA3 marker and the color selection of ADE1 marker (white to red) found on Ad5 PAC16-A/U(E4$^+$, E3$^+$). pLOX-CMV-W9 was cut with SfiI, co-transfected with Ad5 PAC16-A/U(E4$^+$, E3$^+$) into yeast strain YPH857 and selected on SC-Trp, 5FOA plates. Ade$^-$ and CMV-W9$^+$ clones were moved from a yeast background into bacteria by electroporation. Once a CMV-W9 Ad5 clone had been selected using kanamycin selection, the clones were amplified and purified by standard methodologies. The amplified DNA's then were digested with the requisite rare cutter to release the viral genome and used to transfect complementary cells and to rescue infectious viruses.

Example 10

Arm Replacement

The HIS3 arm of a gap-filled adeno vector was mutagenized by inserting a sequence (transgene p38). The plasmid p2Puc was used to modify the HIS3 arm of a gap-filled adeno vector. More specifically, p2PUC was used (a) to introduce an E1 deletion into an Ad5 vector, and (b) by cloning into a polylinker, was used to target a transgene such as the cDNA of p38. Plasmids p2PUC and p2PUC38 were linearized by NotI and transformed separately in a yeast strain that contained Adeno YAC18, using the lithium acetate method. The yeast transformants were selected on selective media lacking lysine and screened on selective media plate lacking histidine. Yeast clones which tested Lys+, but were HIS+, were made into plugs and examined by PFGE. All clones hybridized with total adenovirus DNA. YAC18 showed a positive clone at 65 kb. Yeast strain Y18L/H/T was Lys+, HIS+ and TRP+, and shows a doublet running at 65 kb and 70 kb. Y18+p2PUC showed a positive fragment at 70 kb and Y18+p2PUC+p38 showed a positive clone at 73 kb. Y18 was negative for the Lys probe, positive for the HIS probe and negative for the p38 probe, showing that the HIS3 region is intact and not targeted by p2PUC or p2PUC38. Y18+PUC is positive for Lys, negative for HIS and negative for p38. The data show that the HIS3(5') arm of Y18+PUC had been targeted and replaced by the Lys arm of p2PUC and the increased size is due to the difference between pHISAde-22(8 kb) and p2PUC (13 kb). Y18+p38 is positive for Lys, negative for HIS, positive for p38 and runs slightly higher (73 kb) than the Y18+2PUC. That shows that the HIS3(5') arm of Y18+p38 has been targeted and replaced by the Lys arm of vector p2PUC+p38 and also has targeted the p38 transgene. The size difference between Y18PUC and Y18p38 is due to the 3 kb insert of p38 into the p2PUC, making the total recombinant vector 3 kb larger. Y18L/H/T is positive for Lys and HIS, but is negative for p38. The doublet indicates that there are two vectors present in which one has been targeted with p2PUC (Lys+) and one that has not been targeted (HIS+, Lys−).

Example 11

One Step

Mutations can be introduced into a gap-filled vector without the use of selection against the yeast markers on the arms (i.e., to introduce a mutation in the middle of the gap-filled vector sequences). The ΔE1/E4 1014 strain (His+, Trp+, Ura+ and Ade+) was transformed with the URA/ADE omega vector containing a rare site, I-Ppol, to map the insertion of the omega vector into a vector after targeting. The URA/ADE omega vector was modified to include sequences in the 5' as well as in the 3' region sharing homology with the adenovirus sequences of ADV-5. Following homologous recombination, the resultant clones (e.g., Adeno 802) were isolated and the DNA purified as described above. Adeno 802 was used to transform strain ΔE1/E4 1014 (His+, Trp+, Ura+ and Ade+). ΔE1/E4 1014 (His+, Trp+, Ura− and Ade−) clones were selected on His plates and screened for loss of Ade (red color selection), and Ura with the presence of trp.

Example 12

Two Steps In and Out

A mutation was introduced into a vector without the use of selection against the arms and in which the mutation was made ex vivo of the yeast. A novel deletion (del B) was made by the targeting of a tandem duplication (C) and by the removal of URA 3 and ADE1 by the negative selection of 5FOA on the URA3 yeast marker (Boeke et al. (1984) *Mol. Gen. Genet.* 197:345–346; Brown & Szostak (1983) Meth. Enzymol. 101:278–290).

Example 13

Transition from Yeast to Bacterial System and Circularization of Vector

A gap-filled vector is moved from a yeast background into a bacteria and is circularized using representative cyclization elements according to the invention. Total DNA from clone WΔE1/E4 1014 Lys+Trp+ was purified according to standard protocols. *E. coli* strain N53529 was made electrocompetent by growing the cells to an $OD_{550}$ of 0.7, then collected and washed twice with ice-cold 10% glycerol, flash frozen in a dry-ice ethanol bath and kept at −80° C. Total yeast DNA then was electroporated into N53529 (Cre+) by using a 0.1 cm cuvette at 1,800 V, 200 ohms and 25 mF in a Bio-Rad Gene Pulsar Electroporator. Cells were allowed to recover and clones were selected on kanamycin (5 mg/l) plates. Positive clones were identified, amplified and purified by standard plasmid methods. Adenoviral positive clones were linearized by I-SceI digestion. Following digestion and loss of the arms and the bacterial sequences, purified viral genomes were used to transfect 293 E4/2930F6 cells (Wang et al. (1995) *Gene Therapy* 2:775–783).

Example 14

Engineering and Assembly of a Recombinant Delivery Unit: Adenovirus Assembly

293-E4 cells were plated in 10 cm plates at $2.5 \times 10^6$ cells per plate 48 hours before transfection. One hour prior to transfection, the cells were fed with 10 ml fresh medium (293/TSA medium): DME, 50 ml donor calf serum (10%), 5 ml glutamine and 5 ml pen/strep. 5 μg of DNA was linearized by I-SceI digestion and combined with 293-E4 cells by calcium phosphate precipitation (Wigler et al., (1979) *Cell* 57:777–785). After transfection, cells were incubated at 39° C. for 5 days, harvested and then frozen and thawed three times in a dry ice/ethanol bath. The cells then were centrifuged at 3000× g for 10 mins. and cell lysate was added to fresh 293-E4 cells. Viral DNA then is extracted (see Hirt (1967) *J. Mol. Bio.* 26:365–369). Adenoviral DNA is digested with SmaI and SmaI/I-SceI. Digested DNA is fractionated on 0.7% agarose gel and structural integrity is confirmed.

EQUIVALENTS

Those skilled in the art will recognize, or be able to ascertain, using no more than routine experimentation, numerous equivalents to the specific substances and procedures described herein without departing from the spirit and scope of the instant invention. Such equivalents are considered to be within the scope of the invention, and are covered by the following claims.

All references cited herein and herein incorporated by reference in entirety

What is claimed is:

1. A composition comprising:

a vector for capture, cloning, manipulation, production and delivery of large nucleic acids to a yeast target cell comprising:

(a) a first arm having in sequential order, a first selectable marker, a first cyclization element, and a first segment homologous to the 5' terminus of a target polynucleotide; and (b) a second arm having in sequential order, a second selectable marker, a second cyclization element, and a second segment homologous to the 3' terminus of the target polynucleotide, wherein said vector comprises a polynucleotide sequence homologous to a yeast target polynucleotide sequence for homologous recombination with the target polynucleotide in said yeast target cell, and wherein the target polynucleotide is a polynucleotide of a virus, and said virus is selected from the group consisting of adenovirus, adeno-associated virus, pox virus, papova virus and herpes virus.

2. A bacterial cell comprising the composition of claim 1.

* * * * *